(12) United States Patent
Gadrat et al.

(10) Patent No.: US 12,226,555 B2
(45) Date of Patent: Feb. 18, 2025

(54) SYSTEM AND METHOD FOR TREATING HAEMORRHAGIC FLUID FOR AUTOTRANSFUSION

(71) Applicant: I-SEP, Nantes (FR)

(72) Inventors: Francis Gadrat, Bordeaux (FR); Benoît Decouture, Nantes (FR); Stéphane Chollet, La Chapelle sur Erdre (FR); Patricia Forest-Villegas, Genas (FR); Sylvain Picot, Caluire (FR)

(73) Assignee: I-SEP (FR)

( * ) Notice: Subject to any disclaimer, the term of this patent is extended or adjusted under 35 U.S.C. 154(b) by 510 days.

(21) Appl. No.: 17/622,482

(22) PCT Filed: Jun. 26, 2020

(86) PCT No.: PCT/FR2020/051115
§ 371 (c)(1),
(2) Date: Dec. 23, 2021

(87) PCT Pub. No.: WO2020/260836
PCT Pub. Date: Dec. 30, 2020

(65) Prior Publication Data
US 2022/0241473 A1    Aug. 4, 2022

(30) Foreign Application Priority Data

Jun. 27, 2019   (FR) ...................................... 1907004

(51) Int. Cl.
*A61M 1/02* (2006.01)
*A61M 1/34* (2006.01)

(52) U.S. Cl.
CPC ........ *A61M 1/0281* (2013.01); *A61M 1/0218* (2014.02); *A61M 1/342* (2013.01);
(Continued)

(58) Field of Classification Search
CPC .. A61M 1/0281; A61M 1/0218; A61M 1/342; A61M 2202/0429;
(Continued)

(56) References Cited

U.S. PATENT DOCUMENTS

| 4,886,487 A | 12/1989 | Solem et al. |
| 5,215,519 A | 6/1993 | Shettigar |

(Continued)

FOREIGN PATENT DOCUMENTS

| EP | 0341413 A2 | 11/1989 |
| EP | 0400518 A2 | 12/1990 |

(Continued)

OTHER PUBLICATIONS

Search Report dated dated Oct. 11, 2022 from Office Action for Chinese Application No. 201880090348.0 issued Oct. 24, 2022. 3 pgs.

(Continued)

*Primary Examiner* — Fred Prince
(74) *Attorney, Agent, or Firm* — Lerner David LLP

(57) ABSTRACT

A method and system for treating, by filtration, haemorrhagic fluid contained in a container with a view to subsequent autotransfusion, including at least one step of concentrating by filtration said haemorrhagic fluid in order to increase the concentration of red blood cells in the haemorrhagic fluid to reach a target haematocrit level while at the same time removing from the haemorrhagic fluid a filtrate comprising compounds not desired for autotransfusion, further including:
a preliminary step of measuring the haematocrit level of the haemorrhagic fluid; and a dilution step consisting in adding to the volume of haemorrhagic fluid to be treated a determined volume of dilution fluid, the determined volume of dilution fluid being calculated as (Continued)

a function of the measured haematocrit level of the haemorrhagic fluid and the target haematocrit level.

17 Claims, 6 Drawing Sheets

(52) U.S. Cl.
CPC ............... *A61M 2202/0429* (2013.01); *A61M 2205/3306* (2013.01); *A61M 2205/3334* (2013.01); *A61M 2205/7554* (2013.01); *A61M 2230/207* (2013.01)

(58) Field of Classification Search
CPC .. A61M 2205/3306; A61M 2205/3334; A61M 2205/7554; A61M 2230/207
USPC .................................................. 210/646, 647
See application file for complete search history.

(56) References Cited

U.S. PATENT DOCUMENTS

| | | | |
|---|---|---|---|
| 5,298,016 | A | 3/1994 | Gordon |
| 5,858,238 | A | 1/1999 | McRea et al. |
| 5,876,611 | A * | 3/1999 | Shettigar ............. A61M 1/3692 210/650 |
| 6,251,295 | B1 | 6/2001 | Johnson |
| 6,994,781 | B2 | 2/2006 | Cork et al. |
| 7,686,777 | B2 | 3/2010 | Huang et al. |
| 7,722,557 | B2 | 5/2010 | Sano et al. |
| 8,257,590 | B2 | 9/2012 | Taniguchi et al. |
| 8,388,847 | B2 | 3/2013 | Mitterer et al. |
| 8,569,052 | B2 | 10/2013 | Federspiel et al. |
| 8,758,603 | B2 | 6/2014 | Okazaki |
| 9,341,626 | B2 | 5/2016 | Humes et al. |
| 9,446,074 | B2 | 9/2016 | Kishikawa et al. |
| 2003/0138349 | A1 | 7/2003 | Robinson et al. |
| 2003/0229302 | A1 | 12/2003 | Robinson et al. |
| 2006/0081524 | A1 | 4/2006 | Sengupta et al. |
| 2007/0163942 | A1 | 7/2007 | Tanaka et al. |
| 2012/0226258 | A1 | 9/2012 | Otto et al. |
| 2014/0128838 | A1* | 5/2014 | Satish ................... G06T 7/0012 604/503 |
| 2014/0287502 | A1 | 9/2014 | Taniguchi |
| 2015/0306295 | A1 | 10/2015 | Rovatti |
| 2015/0314057 | A1 | 11/2015 | Labib et al. |
| 2016/0074569 | A1 | 3/2016 | Schuetz et al. |
| 2016/0096148 | A1 | 4/2016 | Schuetz et al. |
| 2016/0158425 | A1 | 6/2016 | Cotton et al. |
| 2016/0158670 | A1 | 6/2016 | Tanizaki et al. |
| 2016/0168529 | A1 | 6/2016 | Taniguchi et al. |
| 2016/0317972 | A1 | 11/2016 | Matsumoto et al. |
| 2016/0339159 | A1 | 11/2016 | Nosaka et al. |

FOREIGN PATENT DOCUMENTS

| | | |
|---|---|---|
| EP | 2461847 A1 | 6/2012 |
| EP | 2631645 A1 | 8/2013 |
| EP | 2735326 A1 | 5/2014 |
| EP | 2735360 A1 | 5/2014 |
| WO | 9301858 A1 | 2/1993 |
| WO | 9829149 A1 | 7/1998 |
| WO | 2019129974 A1 | 7/2019 |

OTHER PUBLICATIONS

French Preliminary Search Report for Application No. 1763308 completed Aug. 2, 2018, 2 pages. [see p. 2, categorizing the cited references].

French Preliminary Search Report for Application No. 1763310 completed Apr. 2, 2018, 2 pages. [see p. 2, categorizing the cited references].

French Preliminary Search Report for Application No. 1907004 dated May 13, 2020, 3 pages. [see p. 3, categorizing the cited references].

Fukunaga, et al., "In Vitro Evaluation Study of the Membrane Autotransfusion System Experimental Prototype: MATS-I," Artificial Organs. Feb. 1, 2000, pp. 95-102, vol. 24, No. 2.

Fukunaga, et al., Preliminary evaluation study of a prototype hollow fiber membrane for the continuous membrane autotransfusion system, Therapeutic Apheresis. Feb. 3, 1999, pp. 63-68, vol. 3, No. 1.

Gadrat, F. et al., U.S. Appl. No. 16/958,458, filed Jun. 26, 2020, titled "System And Method For Treating Haemorrhagic Fluid For Autotransfusion".

Gadrat, F. et al., U.S. Appl. No. 16/958,473, filed Jun. 26, 2020, titled "System And Method For Treating Haemorrhagic Fluid For Autotransfusion".

International Search Report for Application No. PCT/FR2018/053500 mailed Apr. 10, 2019, 2 pages.

International Search Report for Application No. PCT/FR2018/053501 mailed Mar. 7, 2019, 2 pages.

International Search Report for Application No. PCT/FR2020/051115 mailed Oct. 7, 2020, 3 pages.

* cited by examiner

SYSTEM AND METHOD FOR TREATING HAEMORRHAGIC FLUID FOR AUTOTRANSFUSION

CROSS-REFERENCE TO RELATED APPLICATIONS

The present application is a national phase entry under 35 U.S.C. § 371 of International Application No. PCT/FR2020/051115 filed Jun. 26, 2020, which claims priority from French Application No. 1907004 filed Jun. 27, 2019, all of which are incorporated herein by reference.

FIELD OF INVENTION

The present invention relates to the field of the treatment of haemorrhagic fluid such as blood to carry out an autotransfusion on a patient, notably in the course of a surgical intervention.

PRIOR ART

Autotransfusion or autologous transfusion, namely the transfusion into a patient of his or her own blood, is increasingly practiced during surgical interventions since it avoids the incompatibilities that may exist with homologous or allogenic transfusions, that is to say transfusions from the blood of another person, and it notably prevents the transmission of infectious diseases.

In the case of intraoperative autotransfusion, it is advisable to be able to transfuse blood collected directly from the patient almost continuously, that is to say by limiting dead times notably due to the treatment of the blood, this treatment being carried out with a treatment device independently of the patient. Yet, during the collection, in a known manner, this blood already diluted by the operating conditions must also be supplemented with anti-coagulants to enable treatment by an autotransfusion device and to preserve its transfusion quality and the functionalities of the blood elements. These actions appear necessary because, by using a carrier fluid for the collected haemorrhagic blood, the red blood cells may thus be protected from direct physical trauma during mechanical contact with the filters and other tubing. This dilution in a carrier fluid also decreases the contact of the red blood cells with air, thus greatly limiting their haemolysis. Finally, it also makes it possible to control and prevent the coagulating activity of the blood and to avoid the formation of blood clots which would not enable the recovery of blood elements, notably red blood cells. The recovered blood must next be transfused to the patient in order to compensate the loss of blood volume, but important problems are encountered. Indeed, in the case of transfusion of too diluted volumes of blood, it is possible to cause phenomena of hypervolemia by these too important transfused fluid volumes and hypocoagulability syndromes for the same reasons and/or by a too important transfused volume of anti-coagulant if not cleaned.

In addition, during the autotransfusion of blood directly collected and only anticoagulated and haemodiluted, it is possible of transfuse activated or degraded biological substances capable of causing secondary effects. It is possible to find for example histamines, kallikreins or kinins, more or less degraded plasmatic factors which it is best to get rid of or instead small proteins and other cell debris derived from cell trauma.

For intraoperative autotransfusion conditions, the treatment of the blood thus consists in collecting the blood, anti-coagulating it (which leads to a dilution) simultaneously with collection, then prefiltering it in the prefiltration jar and treating it by the treatment device so as to separate the liquid phase from the phase containing cellular elements thus enabling on the one hand a concentration of the phase collected and intended to be transfused and on the other hand a collection of the liquid phase to eliminate. It is advisable to specify that these steps musts be done as quickly as possible since the patient, under intraoperative conditions, generally needs to be transfused urgently.

Different more or less complex and efficient techniques for carrying out autotransfusions on a patient during surgical interventions have been developed.

Autotransfusion systems exist for example based on centrifugation techniques.

Centrifugation of the blood collected in autotransfusion separates the red blood cells (RBC) and platelet rich plasma (PRP) and proteins. A high recovery rate of platelets is thus impossible by this method.

Further, for the process to be rapid, reinforced centrifugation may be carried out but a coat is then going to form at the interface between the red blood cells and the plasma, which is known as buffy coat, which is a mixture of platelets and white blood cells (WBC). This coat is thus unsuitable for direct transfusion.

It is thus necessary to apply complementary treatments to recover the platelets and to eliminate undesired elements such as the buffy coat. Further, when the centrifugation is too strong, there is going to be elimination of the platelets and thus an impoverishment of the quality of the concentrate to transfuse.

The vacuum suction of blood and biological fluids by the surgeon induces trauma of the red blood cells leading to mechanical haemolysis of the most fragile cells. Centrifugation, a known and widely used mechanism in autotransfusion, also leads to slight mechanical haemolysis. During the intraoperative treatment of blood by centrifugation, the red blood cells thus undergo trauma leading to important haemolysis, which can go up to 19%. In urgency mode (reinforced centrifugation to decrease the treatment time), this haemolysis level can reach 33%.

An alternative to current methods for intraoperative treatment of blood by centrifugation is desired because centrifugation, apart from problems of haemolysis, eliminates the majority of platelets (recovery rate less than 10%). This direct loss of cells of interest, directly contributing to primary hemostatis (platelet aggregation at the level of the wound), is problematic during an operation as may easily be understood. Which is why, when the losses are too important, physicians have recourse to the transfusion of labile blood products of which one or more homologous platelet concentrates. A method that would make it possible to conserve and to transfuse the platelets (with preferably a level of recovery greater than 50%) of the patient would consequently be appreciable.

Alternative autotransfusion systems have thus been developed, based on membrane filtration devices. This is for example the case of the autotransfusion systems described in the U.S. Pat. No. 4,886,487, in the U.S. Pat. No. 5,215,519 and in the patent application US 2003/229302, and in the international applications WO 93/01858 and WO 98/29149.

These systems are advantageous in so far as they enable real separation of elements not desired for blood transfusion, without eliminating important elements such as platelets as is the case during centrifugation. However, such systems have a certain number of drawbacks, notably in terms of efficiency.

Cells (RBC, WBC and platelets) exhibit important membrane deformability enabling them to pass through blood micro-vessels or wounds. Nevertheless, during membrane filtration, a drop in the filtration flow is observed throughout the process. The drop off in flow may be explained by several factors, namely, adsorption, steric hindrance, the effects of viscosity, obstruction and clogging of the pores, as well as the concentration gradient at the membrane/solution interface.

In the case of filtration, the size of the pores and the hydrophilicity of the materials must be controlled in order to allow these cells to pass through or not. In the case of the use of a membrane with pores of diameters less than 10 µm, in particular less than 1 µm, the clogging of the membranes by the cells is obligatory in frontal filtration, hence the necessity of tangential filtration. Platelets also have high adhesive power after activation and have a tendency to adsorb on the surface of the membranes or plasmatic proteins and clog up the membranes.

Tangential filtration is subjected to a quantity of material being able to pass through the membrane per unit of time, which limits in general the speed of treatment. This is referred to as transmembrane flow rate or filtration coefficient. However, a patient suffering from a massive haemorrhage cannot have his loss of chance coefficient increased on account of a longer filtration time. It is thus vital that the time for treating blood intraoperatively by filtration is comparable to the conventional method of centrifugation, where a separation of red blood cells and plasma may be done in a rapid time of 4-6 minutes for a collected volume of blood of 500 ml.

In the same way for the treatment time, the performances of treatment by filtration membrane must be at least comparable with the intraoperative treatment of blood by the centrifugation method (level of recovery of RBC greater than 80%, quantity of heparin less than 0.5 IU/ml).

DESCRIPTION OF THE INVENTION

There exists today a need for an improved system for treating blood for autotransfusion, notably making it possible to resolve at least one of the aforesaid drawbacks.

An aim of the present invention is also to propose a blood treatment system for autotransfusion that it easy to use, intuitive, in such a way as to be able to be used by professionals with little or no training.

To this end, a system is proposed for treating haemorrhagic fluid taken beforehand from a patient with a view to autotransfusion, including a unit for treating the haemorrhagic fluid, said treatment unit comprising:
 a filtration device for tangential filtration comprising a filtration membrane arranged in a case in such a way as to separate an intake chamber from a discharge chamber, the intake chamber and the discharge chamber each having an inlet and an outlet for fluids;
 a treatment bag having an inlet and an outlet fluidically connected by a recirculation line to the outlet and to the inlet of the intake chamber of the filtration device, respectively, enabling circulation of the haemorrhagic fluid in the recirculation line in a direction going from the outlet of the treatment bag to the inlet of the treatment bag through the intake chamber of the filtration device;
 an intake line fluidically connected to the recirculation line between the outlet of the treatment bag and the inlet of the intake chamber of the filtration device making it possible to supply the treatment unit with the collected haemorrhagic fluid with a view to filtration through the filtration membrane of the filtration device in order to remove from the haemorrhagic fluid a filtrate comprising compounds not desired for autotransfusion;
 a transfusion line fluidically connected to the recirculation line between the outlet of the treatment bag and the inlet of the intake chamber of the filtration device making it possible to recover the treated haemorrhagic fluid contained in said treatment bag;
 a discharge line fluidically connected to the outlet of the discharge chamber of the filtration device so as to discharge the filtrate having passed through the filtration membrane from the intake chamber;
characterised in that the treatment unit further comprises
 a cleaning line fluidically connected to the inlet of the discharge chamber of the filtration device for conveying a cleaning fluid into said discharge chamber; and
 a first flow regulation member arranged for flow regulation in the cleaning line and a second flow regulation member arranged for flow regulation in the discharge line in such a way as to be able to control the pressure of cleaning fluid in the discharge chamber.

Preferred but non-limiting aspects of this treatment system, taken alone or in combination, are the following:
 the cleaning line is further fluidically connected to the recirculation line at a first position between the outlet of the treatment bag and the inlet of the intake chamber of the filtration device, the treatment unit further comprising a dilution line intended to convey a dilution fluid into the treatment unit, the dilution line being fluidically connected to the recirculation line at a second position between the outlet of the treatment bag and the inlet of the intake chamber of the filtration device, the dilution fluid being able to be used as cleaning fluid.
 the treatment unit comprises a third flow regulation member arranged for flow regulation in the dilution line, a fourth flow regulation member arranged for flow regulation in the recirculation line at the outlet of the treatment bag, and a fifth flow regulation member arranged for flow regulation in the recirculation line at the inlet of the intake chamber of the filtration device.
 the second position is situated upstream of the first position in the direction of circulation of fluid in the recirculation line during treatment of the haemorrhagic fluid.
 the system comprises a single peristaltic pump arranged so as to make the haemorrhagic fluid circulate in the recirculation line in a direction going from the outlet of the treatment bag to the inlet of the treatment bag through the intake chamber of the filtration device, said peristaltic pump being positioned in the recirculation line between the outlet of the treatment bag and the inlet of the intake chamber of the filtration device between the second position and the first position.
 the system comprises at least one peristaltic pump arranged in such a way as to circulate the haemorrhagic fluid in the recirculation line in a direction going from the outlet of the treatment bag to the inlet of the treatment bag through the intake chamber of the filtration device.
 the treatment bag comprises a separator device being able to be actuated to separate the treatment bag into a first treatment chamber on the side of the inlet of the treatment bag and a second treatment chamber on the side of the outlet of the treatment bag.

- the treatment bag has a substantially parallelepiped shape with the inlet and the outlet on either side of the treatment bag along a diagonal, the treatment bag further having an inner cavity having a tapered shape on the side of the outlet.
- the filtration membrane of the filtration device is a filtration membrane with hollow fibres, said hollow fibres forming the filtration membrane extending longitudinally into the case.
- the filtration membrane with hollow fibres of the filtration device comprises hollow fibres formed from a mixture of polyester sulphone and polyvinyl pyrrolidone.
- the filtration membrane of the filtration device has an overall porosity comprised between 0.1 µm and 1 µm, preferably of the order of 0.6 µm.
- the filtration membrane of the filtration device has an overall filtration surface area comprised between 0.1 m² and 1 m², and preferably comprised between 0.2 m² and 0.6 m².
- the treatment unit comprises a sixth flow regulation member arranged for flow regulation in the transfusion line.
- the treatment system comprises a plurality of regulation valves, each regulation valve being respectively intended to cooperate with one of the regulation members in order to regulate the corresponding flow.
- the treatment unit comprises a template enabling fixation of the intake line, the discharge line, the recirculation line, the transfusion line and the cleaning line.
- the treatment system comprises a support unit, the template of the treatment unit having a fool proof shape making it possible to couple the treatment unit to the support unit according to a unique positioning, preferably removably.
- the support unit forms a horizontal support plane, the filtration device of the treatment unit being intended to be coupled to the support unit such that the hollow fibres of the filtration membrane extend along a direction not comprised in the horizontal support plane.
- the treatment system comprises a transfusion unit, said transfusion unit comprising a transfusion bag having an inlet intended to be connected to the transfusion line in order to collect the treated haemorrhagic fluid coming from the treatment bag before transfusion to the patient.
- the treatment system comprises a filtrate recovery unit, said recovery unit comprising a recovery bag having an inlet intended to be fluidically connected to the discharge line, said recovery bag further being intended to be coupled to a device for depressurising the recovery bag in such a way as to circulate the filtrate from the discharge chamber of the filtration device to the recovery bag through the discharge line.
- the treatment system comprises a filtrate recovery unit, said recovery unit comprising a recovery bag having an inlet intended to be fluidically connected to the discharge line, said recovery bag further being arranged with respect to the filtration device of the treatment unit to create a depressurisation of the recovery bag with respect to the filtration device in such a way as to circulate the filtrate from the discharge chamber of the filtration device to the recovery bag through the discharge line.
- the treatment system comprises a haemorrhagic fluid collection unit comprising a receptacle for collecting the haemorrhagic fluid collected beforehand from the patient, said collection receptacle having an outlet fluidically connected to the intake line, said collection receptacle preferably integrating a prefiltration device making it possible to carry out a prefiltration of the haemorrhagic fluid before being transmitted into the treatment unit.
- the treatment system further comprises an additional prefiltration device placed in the intake line.

A method is also proposed for using this system for treating haemorrhagic fluid taken beforehand from a patient with a view to subsequent autotransfusion wherein, after partial or total treatment of the haemorrhagic fluid with the filtration device, a cleaning of the filtration membrane is carried out by creating a transmembrane counter-flow, the counter-flow being created by obstructing the discharge line at the level of the second flow regulation member and by injecting the cleaning fluid into the discharge chamber from the cleaning line, the pressure created in the discharge chamber by the injection of the cleaning fluid creating a counter-flow through the filtration membrane making it possible to disbond all or part of the elements retained on the filtration membrane.

Preferred but non-limiting aspects of this method for using the treatment system, taken alone or in combination, are the following:
- the counter-flow cleaning is carried out at regular intervals during the treatment of a determined volume of haemorrhagic fluid.
- the counter-flow cleaning is carried out after the total treatment of a determined volume of haemorrhagic fluid.
- the counter-flow cleaning is carried out by varying the speed of circulation of the cleaning fluid, in particular by increasing and decreasing said speed of circulation of the cleaning fluid.
- a determined volume of haemorrhagic fluid coming from the intake line is treated by circulating it in the circulation line in order to pass through the filtration device several times to remove compounds not desired for autotransfusion, the treatment bag making it possible to maintain a flow having a continuous flow rate in the circulation line whatever the volume of haemorrhagic fluid to be treated.
- during the treatment of a determined volume of haemorrhagic fluid, the outlet of the treatment bag is obstructed, then one injects into the circulation line a dilution fluid intended to pass through the filtration device in such a way as to eliminate the haemorrhagic fluid present in the circulation line, then the treated haemorrhagic fluid present in the treatment bag is isolated when the fluid present in the circulation line has a haematocrit level less than a threshold value.

According to another preferred but non-limiting aspect of this method for using the treatment system, taken alone or in combination with the preceding aspects, —before and/or after counter-flow cleaning—a cleaning of the filtration membrane is carried out by rinsing, the rinsing being operated by obstructing the outlet of the treatment bag, by obstructing the discharge line at the level of the outlet of the discharge chamber of the filtration device, and by injecting into the intake chamber a dilution fluid intended to pass through the filtration device.

A system for treating haemorrhagic fluid collected beforehand from a patient with a view to autotransfusion is furthermore proposed, including a unit for treating the haemorrhagic fluid, said treatment unit comprising:
- a filtration device comprising a filtration membrane for tangential filtration arranged in a case in such a way as to separate an intake chamber from a discharge chamber, the intake chamber and the discharge chamber each having an inlet and an outlet for fluids;

a treatment bag having an inlet and an outlet fluidically connected by a recirculation line to the outlet and to the inlet of the intake chamber of the filtration device, respectively, enabling a circulation of the haemorrhagic fluid in the recirculation line in a direction going from the outlet of the treatment bag to the inlet of the treatment bag through the intake chamber of the filtration device;

an intake line fluidically connected to the recirculation line between the outlet of the treatment bag and the inlet of the intake chamber of the filtration device making it possible to supply the treatment unit with the collected haemorrhagic fluid with a view to filtration through the filtration membrane of the filtration device in order to remove from the haemorrhagic fluid a filtrate comprising compounds not desired for autotransfusion;

a transfusion line fluidically connected to the recirculation line between the outlet of the treatment bag and the inlet of the intake chamber of the filtration device making it possible to recover the treated haemorrhagic fluid contained in said treatment bag;

a discharge line fluidically connected to the outlet of the discharge chamber of the filtration device so as to discharge the filtrate having passed through the filtration membrane from the intake chamber;

characterised in that the treatment unit further comprises a first flow regulation member arranged for flow regulation in the recirculation line at the outlet of the treatment bag, and a dilution line intended to convey a dilution fluid into the treatment unit, the dilution line being fluidically connected to the recirculation line at a position between the outlet of the treatment bag and the inlet of the intake chamber of the filtration device.

Preferred but non-limiting aspects of this treatment system, taken alone or in combination, are the following:

the treatment unit comprises a haematocrit sensor arranged to measure a haematocrit level of the haemorrhagic fluid circulating in the treatment unit.

the treatment system further comprises a device for controlling the dilution line programmed to control the dilution fluid to convey into the treatment unit as a function of the haematocrit level measured by the haematocrit sensor.

an optical sensor is arranged at the level of the inlet of the treatment bag to detect the nature of the fluid arriving at the level of the inlet.

the treatment bag comprises a separator device being able to be actuated to separate the treatment bag into a first treatment chamber on the side of the inlet of the treatment bag and a second treatment chamber on the side of the outlet of the treatment bag.

the treatment unit comprises a second flow regulation member arranged for flow regulation in the dilution line, and a third flow regulation member arranged for flow regulation in the recirculation line at the inlet of the intake chamber of the filtration device.

the treatment bag has a substantially parallelepiped shape with the inlet and the outlet on either side of the treatment bag along a diagonal, the treatment bag further having an inner cavity having a tapering shape on the side of the outlet.

the filtration membrane of the filtration device is a filtration membrane with hollow fibres, said hollow fibres forming the filtration membrane extending longitudinally into the case.

the filtration membrane with hollow fibres of the filtration device comprises hollow fibres formed from a mixture of polyester sulphone and polyvinyl pyrrolidone.

the filtration membrane of the filtration device has an overall porosity comprised between 0.1 µm and 1 µm, preferably of the order of 0.6 µm.

the filtration membrane of the filtration device has an overall filtration surface area comprised between 0.1 m$^2$ and 1 m$^2$, and preferably comprised between 0.2 m$^2$ and 0.6 m$^2$.

the treatment system comprises at least one peristaltic pump arranged in such a way as to circulate the haemorrhagic fluid in the recirculation line in a direction going from the outlet of the treatment bag to the inlet of the treatment bag through the intake chamber of the filtration device.

the treatment system comprises a plurality of regulation valves, each regulation valve being respectively intended to cooperate with one of the regulation members in order to regulate the corresponding flow.

the treatment unit comprises a template enabling a fixation of the intake line, the discharge line, the recirculation line, the dilution line, and the transfusion line.

the treatment system comprises a support unit, the template of the treatment unit having a fool proof shape making it possible to couple the treatment unit to the support unit according to a unique positioning.

the support unit forms a horizontal support plane, the filtration device of the treatment unit being intended to be coupled to the support unit such that the hollow fibres of the filtration membrane extend along a direction not comprised in the horizontal support plane.

the treatment system comprises a transfusion unit, said transfusion unit comprising a transfusion bag having an inlet intended to be connected to the transfusion line in order to collect the treated haemorrhagic fluid coming from the treatment bag before transfusion to the patient.

the treatment system comprises a filtrate recovery unit, said recovery unit comprising a recovery bag having an inlet intended to be fluidically connected to the discharge line, said recovery bag being further intended to be coupled to a device for depressurising the recovery bag in such a way as to circulate the filtrate from the discharge chamber of the filtration device to the recovery bag through the discharge line.

the treatment system comprises a filtrate recovery unit, said recovery unit comprising a recovery bag having an inlet intended to be fluidically connected to the discharge line, said recovery bag being further arranged with respect to the filtration device of the treatment unit to create a depressurisation of the recovery bag with respect to the filtration device in such a way as to circulate the filtrate from the discharge chamber of the filtration device to the recovery bag through the discharge line.

the treatment system comprises a unit for collecting the haemorrhagic fluid comprising a receptable for collecting the haemorrhagic fluid taken beforehand from the patient, said collection receptacle having an outlet fluidically connected to the intake line, said collection receptacle preferably integrating a prefiltration device making it possible to carry out a prefiltration of the haemorrhagic fluid before being transmitted into the treatment unit.

the treatment system further comprises an additional prefiltration device placed in the intake line.

A method is also proposed for using this system for treating haemorrhagic fluid taken beforehand from a patient with a view to subsequent autotransfusion wherein, after partial or total treatment of the haemorrhagic fluid with the filtration device, a dilution fluid is injected from the dilution line into the circulation line in order to pass through the filtration device.

According to a preferred aspect of this method for using the treatment system, a cleaning of the filtration membrane is carried out by rinsing, the rinsing being operated by obstructing the outlet of the treatment bag at the level of the first flow regulation member, by obstructing the discharge line at the level of the second flow regulation member and by injecting the cleaning fluid into the intake chamber from the dilution line.

In this case, the rinsing may be stopped as soon as the optical sensor detects the presence of the dilution fluid.

In a preferred manner, before rinsing, it is possible to control the separator device to isolate the haemorrhagic fluid treated in the second treatment chamber.

According to another preferred aspect of this method for using the treatment system, in a complementary or alternative manner, a dilution of the haemorrhagic fluid contained in the treatment system is carried out, the dilution being operated by obstructing the outlet of the treatment bag at the level of the first flow regulation member, then by injecting the cleaning fluid into the intake chamber from the dilution line, then by isolating the treated haemorrhagic fluid present in the treatment bag when the fluid present in the circulation line has a haematocrit level less than a threshold value.

A method is finally proposed for treating, by filtration, haemorrhagic fluid contained in a container with a view to subsequent autotransfusion, comprising at least one step of concentrating by filtration said haemorrhagic fluid in order to increase the concentration of red blood cells in the haemorrhagic fluid to reach a target haematocrit level while at the same time removing from the haemorrhagic fluid a filtrate comprising compounds not desired for autotransfusion, characterised in that it further comprises the following steps:
  a preliminary step of measuring the haematocrit level of the haemorrhagic fluid; and
  a dilution step consisting in adding to the volume of haemorrhagic fluid to be treated a determined volume of dilution fluid, said determined volume of dilution fluid being calculated as a function of the measured haematocrit level of said haemorrhagic fluid and the target haematocrit level.

Preferably, the haemorrhagic fluid contained in a container is taken beforehand from a patient. After having been treated according to the method of treatment by filtration, the treated haemorrhagic fluid may be transfused, preferably to the patient from whom it has been taken. It is to be noted that the method for treating haemorrhagic fluid by filtration is carried out without connection with the patient.

Preferred but non-limiting aspects to the method of treatment by filtration, taken alone or in combination, are the following:
  the dilution step is carried out before a step of concentration by filtration in order to increase the volume of haemorrhagic fluid to be treated and thus increase the volume of filtrate comprising compounds not desired for autotransfusion obtained during the step of concentration by filtration for a given target haematocrit level.

the treatment is further parameterised to obtain a concentration of compounds not desired for autotransfusion less than a target concentration of compounds not desired for autotransfusion, said target concentration of compounds not desired for autotransfusion also being used to calculate the determined volume of dilution fluid for the dilution step.

the initial concentration of compounds not desired for autotransfusion of the haemorrhagic fluid to be treated is also used to calculate the determined volume of dilution fluid for the dilution step.

the number of concentration by filtration steps and dilution steps is optimised to minimise the overall treatment time of the haemorrhagic fluid.

the optimisation is achieved by setting a maximum value of volume of dilution fluid used for each dilution step and by increasing the number of steps of concentration by filtration.

the treatment method comprises several steps of concentration by filtration each being preceded by a dilution step, wherein during the final dilution step the determined volume of dilution fluid is calculated as a function of the measured haematocrit level of said haemorrhagic fluid, the volume of haemorrhagic fluid to be treated, the target haematocrit level, and the target concentration of compounds not desired for autotransfusion, whereas during the preceding dilution steps, the determined volume of dilution fluid is fixed.

the treatment method comprises several steps of concentration by filtration each being preceded by a dilution step, wherein for each dilution step the determined volume of dilution fluid is calculated as a function of the measured haematocrit level of said haemorrhagic fluid, the volume of haemorrhagic fluid to be treated, the target haematocrit level, and the target concentration of compounds not desired for autotransfusion.

the treatment method comprises at least two steps of concentration by filtration each being preceded by a dilution step, and preferably exactly two steps of concentration by filtration each being preceded by a dilution step (i.e. in total two dilution steps each preceding a concentration step).

the dilution volume of the first dilution step preceding the first concentration step is provided to eliminate at least 75% of compounds not desired for autotransfusion present in the haemorrhagic fluid before the first dilution and concentration steps.

the treatment method comprises at least three steps of concentration by filtration each being preceded by a dilution step, and preferably exactly three steps of concentration by filtration each being preceded by a dilution step (i.e. in total three dilution steps each preceding a concentration step).

the dilution volume of the first dilution step preceding the first concentration step is provided to eliminate at least 65% of compounds not desired for autotransfusion present in the haemorrhagic fluid before the first dilution and concentration steps, and the dilution volume of the second dilution step preceding the second concentration step is provided to also eliminate at least 65% of compounds not desired for autotransfusion present in the haemorrhagic fluid before the second dilution and concentration steps.

the treatment method comprises a first step of concentration by filtration carried out without prior dilution of the volume of haemorrhagic fluid to be treated, followed at least by a dilution step and a step of concentration by filtration.

the treatment method comprises a first step of simple filtration without concentration and without prior dilution of the volume of haemorrhagic fluid to be treated, followed at least by a dilution step and a step of concentration by filtration.

according to the proposed treatment method:
  if the haematocrit level of the haemorrhagic fluid is greater than a threshold haematocrit level value, a first step of the treatment consists in a simple filtration without concentration and without prior dilution of the volume of haemorrhagic fluid to be treated; and
  if the haematocrit level of the haemorrhagic fluid is less than or equal to the threshold haematocrit level value, the first step of the treatment consists in a simple concentration by filtration without prior dilution of the volume of haemorrhagic fluid to be treated.

the volume of haemorrhagic fluid to be treated is determined as a function of the measured haematocrit level of said haemorrhagic fluid and the target haematocrit level.

DESCRIPTION OF THE FIGURES

Other characteristics and advantages of the invention will become clearer from the description that follows, which is purely illustrative and non-limiting and which should be read with regard to the appended drawings, in which.

DETAILED DESCRIPTION OF THE INVENTION

Figure 1:
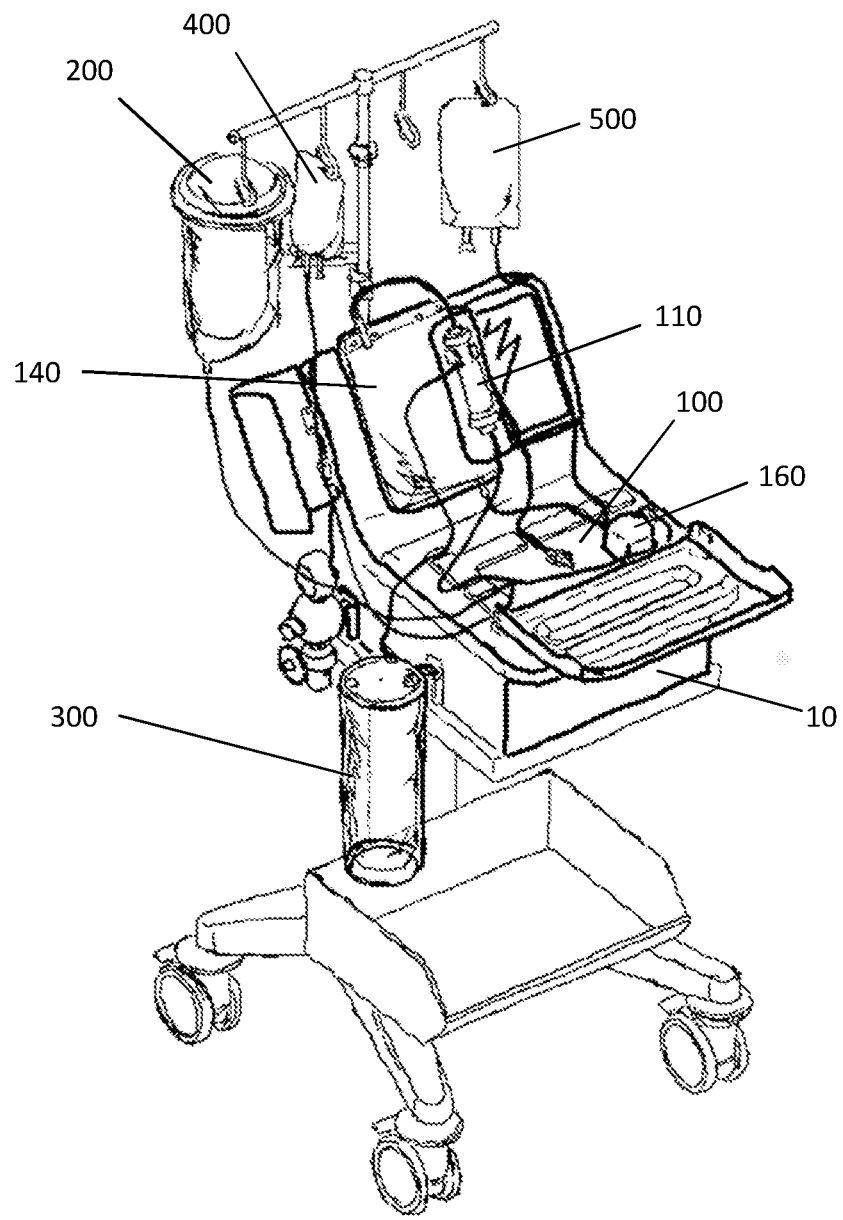
FIG. 1 is a schematic perspective view of a treatment system according to the invention.

Description of the System for Treating a Haemorrhagic Fluid with a View to Autotransfusion FIG. 1 illustrates a non-limiting example of a system for treating a haemorrhagic fluid, notably blood, of a patient with a view notably to autotransfusion.

The proposed treatment system comprises a certain number of functional units, removable with respect to each other to facilitate the use thereof by practitioners, notably during a surgical intervention.

One of the particularities of the proposed treatment system resides in the blood treatment unit 100 that will be described in detail hereafter.

The proposed treatment system preferably comprises a support unit 10 which may be in various forms, with notably as represented in FIG. 1 a main support body being able to be mounted on wheels. Preferably, the support unit 10 integrates the non-consumable elements of the treatment system, that is to say those being able to be reused during several successive treatment cycles, in particular the elements of the system not being in direct contact with the haemorrhagic fluid of the patient or any other substance that could lead to contamination.

The support unit 10 may notably integrate data processing means, in the form of one or more processors for example, but also control means making it possible to control the treatment of the haemorrhagic fluid as a function of predetermined treatment parameters and/or as a function of control information input by the user of the system. In this respect, the support unit 10 may include control information input means, such as a keyboard, tactile actuators, a voice recognition system or others. Preferably, information broadcasting means are also provided to inform the user of the treatment cycle, these information broadcasting means being able to be visual, audible and/or tactile, including for example a screen, lamps or light emitting diodes, a loudspeaker, a vibrator or others.

The support unit 10 also preferably integrates elements for the energy supply, notably electrical, of the treatment system. The support unit 10 could integrate a battery to supply energy to the system, and whatever the case it comprises electrical connectors making it possible to connect said support unit 10 to an electric socket, for example a wall socket of a hospital.

The circulation of fluids in the treatment system is carried out by fluid drive means which are integrated in the support unit 10 or which are external.

As fluid drive means, one or more peristaltic pumps 160 may for example be provided making it possible to move the fluids present in a circulation circuit of the treatment system, in a specific direction of displacement of the fluid, but also possibly in the opposite direction.

Preferably, said peristaltic pump(s) are integrated in the support unit 10, where they may be directly supplied electrically. The fluid drive means are preferably provided to enable circulation of the haemorrhagic fluid in the treatment unit 100 with a flow rate comprised between 10 ml/min and 4000 ml/min, preferably between 100 ml/min to 2000 ml/min, and further preferably between 200 ml/min to 1400 ml/min.

Among fluid drive means, vacuum systems may also be provided, which are connected up to the fluid circulation circuit to create depressurisations favouring the displacement of the fluid in the circulation circuit in a specific direction of displacement. In this respect, there could be integrated in the treatment system, and more specifically in the support unit 10, one or more vacuum pumps to create the required depressurisations. It may also be provided that the treatment system comprises connectors enabling connection with wall vacuum sockets in the place where the treatment system is used, and also vacuum regulators so that the vacuum can be controlled specifically. Preferably, means making it possible to apply a vacuum of 0 to −100 kPa are provided.

The support unit 10 may further integrate other elements being able to be reused during several successive treatment cycles and which are functionally linked to the operations conducted by the treatment unit 100 which will be detailed hereafter.

Thus, the support unit may integrate flow regulation valves, such as solenoid valves operating for example with electromagnets or stepper motors, which are arranged to cooperate with the pipes of the treatment unit 100 to enable regulation of the flow of the fluid circulating in said treatment unit 100.

Sensors may also be provided making it possible to monitor the evolution of the treatment during a specific treatment cycle. Such sensors may for example include pressure sensors, weighing devices, sensors notably optical sensors for calculating the haematocrit level (e.g. to calculate the haematocrit level of the fluid circulating in the treatment unit).

As specified above, these reusable elements are preferably integrated in the support unit 10 but it could also be envisaged that the treatment unit 100 integrates one or more thereof.

The treatment system further comprises a haemorrhagic fluid collection unit 200 which is suited to be positioned on the support unit 10 as illustrated in FIG. 1.

Such a collection unit 200 comprises a receptacle for collecting 210 the haemorrhagic fluid taken from the patient, for example during a surgical intervention, or beforehand.

Figure 2:
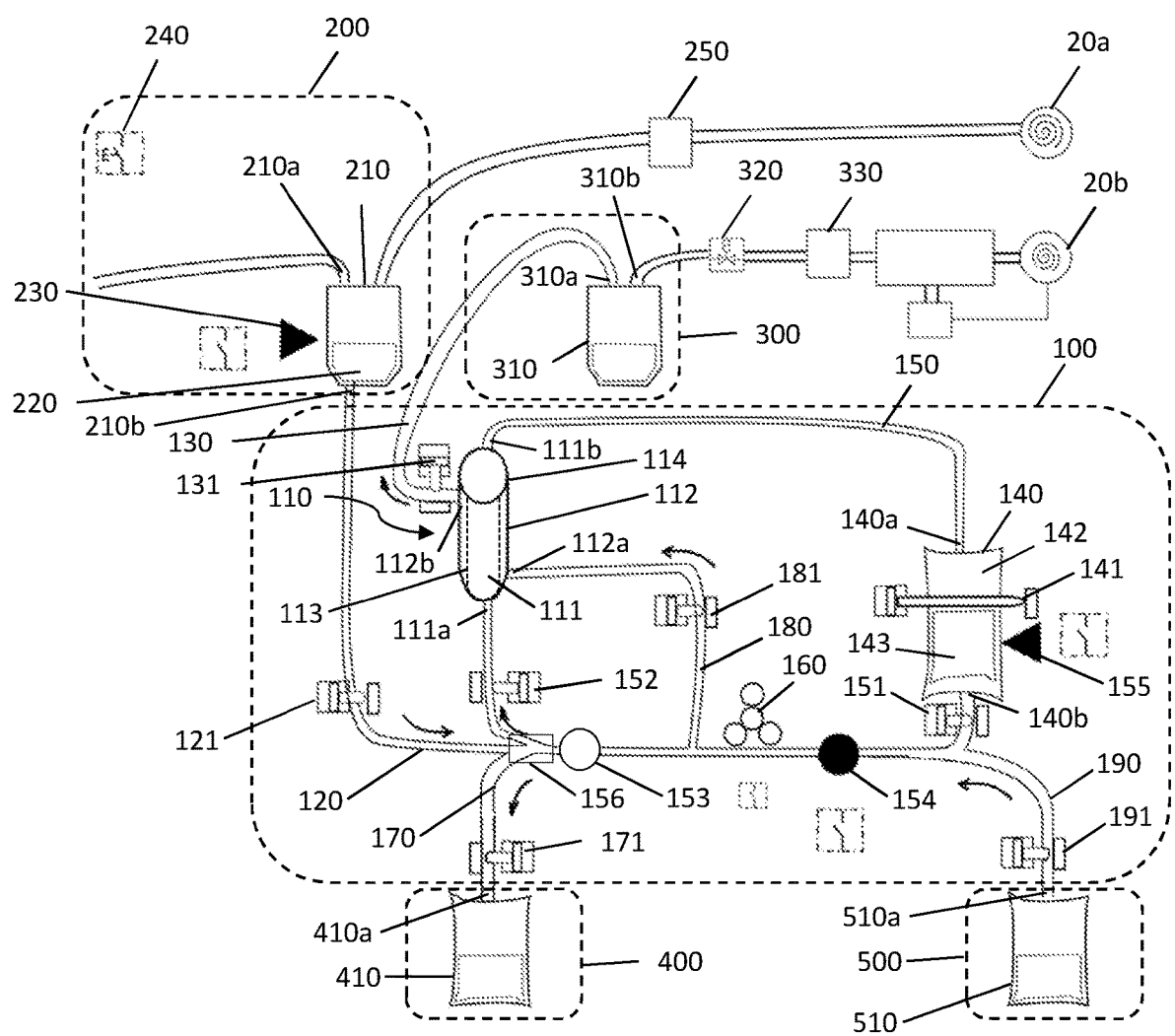
FIG. 2 is a schematic representation of a first arrangement of fluidic connections for the treatment system according to the invention.

As may be seen illustrated in FIG. 2, this collection receptacle 210 has an outlet 210*b* fluidically connected to an intake line 120 provided in the treatment unit 100.

It also comprises an inlet 210*a* intended to be coupled to blood collection means known per se, generally comprising a suction cannula for sucking up haemorrhagic fluid and means for dosing diluents and anticoagulants notably. A specific source of these diluents and/or anticoagulants, such as for example a heparinised crystalloid composition, could be connected directly to the inlet 210*a* of the collection receptacle 210.

Further preferably, the collection receptacle 210 integrates a prefiltration device 220 making it possible to carry out a prefiltration of the collected haemorrhagic fluid before being transmitted into the treatment unit 100. Such a prefiltration is generally intended to filter out particles of relatively large dimensions, to remove for example blood clots, pieces of bone or even pieces of tissues present in the collected haemorrhagic fluid.

The prefiltration is notably carried out to retain particles having a size greater than several tens of micrometres.

It is possible for example to use a prefiltration device 220 of frontal filtration type having a porosity gradient, to retain particles of decreasing sizes, the porosity gradient going for example progressively from 150 µm to 40 µm.

This prefiltration device 220 may for example be a multilayer type filter, more specifically with a woven mesh layer to retain the largest elements, an unwoven mesh layer of which the thickness will make it possible to retain by steric hindrance elements of smaller size, and a final finely woven layer to retain the smallest elements.

In a preferred manner, the collection unit 200 is further connected to a vacuum source, for example to a wall vacuum socket 20*a* via a vacuum regulator 250, to optimise prefiltration with the prefiltration device 220.

A weighing system 230 may further be provided in the collection unit 200, such as a force sensor forming weight indicator, provided to measure the quantity of collected haemorrhagic fluid present in the collection receptacle 210. This weighing system 230 is going to make it possible to give information to control the treatment cycle, making it possible for example to start a treatment cycle when the collection receptacle 210 contains sufficient haemorrhagic fluid to start a treatment cycle. The weighing system 230 also makes it possible to control the quantity of haemorrhagic fluid injected into the treatment unit 100.

The treatment system further comprises a transfusion unit 400 which is intended to be arranged on the support unit 10 and coupled to the transfusion line 170 of the treatment unit 100.

More specifically, the transfusion unit 400 comprises a transfusion bag 410 having an inlet 410*a* intended to be connected to the transfusion line 170 in order to collect the treated haemorrhagic fluid coming from a treatment bag 140 integrated in the treatment unit 100, before transfusion to the patient. More specifically, when it is wished to carry out transfusion into the patient, it is advisable to disconnect the transfusion bag 410 from the treatment system and to connect it to the patient for transfusion of the treated haemorrhagic fluid.

The treatment system also comprises a recovery unit 300 also mounted on the support unit 10 and intended to recover the filtrate coming from the treatment unit 100, that is to say the wastes collected from the haemorrhagic fluid unsuited for transfusion to the patient.

This recovery unit 300 thus comprises a recovery bag 310 having an inlet 310*a* intended to be fluidically connected to the discharge line 130 of the treatment unit 100.

Preferentially, the recovery bag 310 is further provided to be depressurised in such a way as to drive the fluid circulating from the discharge line 130 to said recovery bag 310.

For this purpose, the recovery bag 310 may be coupled to a vacuum device, such as for example a vacuum system using a wall vacuum socket 20*b* and a vacuum regulator 330 and/or an autonomous system comprising at least a vacuum pump and an electronic regulator. A fine control of the applied vacuum makes it possible to control the applied depressurisation to avoid it either being too low and that the treatment is slowed down, or too high, which could damage the red blood cells or the filter. A cut-off and air venting valve 320 may also be provided for disengaging the vacuum system as needs be.

Alternatively or in addition, the depressurisation of the recovery bag 310 may be created by a specific arrangement with respect to the treatment unit 100, notably by a difference in height between the two units. As may be seen represented in FIG. 1 for example, the recovery unit 300 is preferably arranged in the lower part of the support unit 10, close to the wheels for example, whereas the treatment unit 100 is arranged in the upper part or, to say the least, at a level higher than the recovery unit 300. It is to be noted that a depressurisation of the recovery bag 310 by the simple arrangement of the elements between them, without use of an artificial vacuum (with a vacuum pump for example) may be advantageous to limit risks of haemolysis notably.

A vertical distance separating the treatment unit 100 from the recovery unit 300 of at least 10 cm may for example be provided, preferably comprised between 20 cm and 100 cm, preferably comprised between 30 cm and 70 cm, and further preferably comprised between 30 cm and 60 cm.

Specifically, when the depressurisation of the recovery bag 310 is uniquely created by the specific arrangement with respect to the treatment unit 100, the vertical distance separating the treatment unit 100 from the recovery unit 300 is preferably chosen greater than 30 cm, for example comprised between 50 cm and 70 cm, preferably comprised between 60 cm and 65 cm, and further preferably of the order of 65 cm. One of the particularities of the proposed treatment system resides in the treatment unit 100, removable with respect to the support unit 10, in such a way as to be able to replace easily and rapidly, for each new patient, and having a configuration enabling a rapid treatment of the collected haemorrhagic fluid to be carried out without having the drawbacks of the systems existing in the prior art, notably those based on centrifugation.

It is to be noted that all the elements of the treatment system which are intended to be in contact with the haemorrhagic fluid to be treated, which are qualified as consumable, are removable with respect to the support unit 10, and may thus be replaced very easily. Apart from the treatment unit 100, this concerns notably the collection unit 200, the recovery unit 300, and the transfusion unit 400.

The proposed treatment unit 100 is provided to enable efficient treatment of the haemorrhagic fluid of a patient and to be used several times successively for a same patient, in order to be able to carry out several treatment cycles and thus to treat a greater quantity of haemorrhagic fluid.

As explained above, it is preferable to carry out a tangential filtration, that is to say a filtration where the haemorrhagic fluid to filter circulates parallel to a filtration membrane and is filtered on contact with this filtration membrane.

To this end, the proposed treatment unit 100 thus comprises a filtration device 110 for tangential filtration having a filtration membrane 113 arranged in a case 114 in such a way as to separate an intake chamber 111 from a discharge chamber 112, the intake chamber 111 and the discharge chamber 112 each having an inlet (111a; 112a) and an outlet (111b; 112b) for fluids. The haemorrhagic fluid to be treated circulates in the intake chamber 111 from the inlet 111a to the outlet 111b and undergoes a tangential filtration through the filtration membrane 113 in order to remove from the haemorrhagic fluid a filtrate comprising compounds not desired for autotransfusion. The filtrate passes through the filtration membrane 113 into the discharge chamber 112.

Preferentially, the filtration device 110 for tangential filtration comprises a filtration membrane 113 with hollow fibres arranged in the case 114, said hollow fibres forming the filtration membrane extending longitudinally into the case 114. The remainder of the description is made essentially with reference to a treatment unit having a filtration device 110 with a filtration membrane 113 with hollow fibres but the corresponding teaching could apply to all types of tangential filtration devices, notably vis-à-vis problems of clogging following successive filtrations.

In a preferred manner, the filtration membrane 113 with hollow fibres of the filtration device 110 comprises fibres formed of a material having properties favouring its hydrophilicity. The fact that the filtration membrane 113 has increased hydrophilicity notably makes it possible to reduce the phenomenon of clogging of the membrane which occurs as filtration proceeds. Reducing fouling of the filtration membrane 113 makes it possible to maintain increased efficiency of the filtration device 110.

Thus, preferably the hollow fibres of the filtration membrane 113 are formed from a mixture of polyester sulphone (PES) and polyvinyl pyrrolidone (PVP). For example, a PES membrane that has been mixed with PVP before extrusion of the fibre is provided. The base material of the hollow fibres could also be chosen from among other biocompatible and commonly used materials such as blood filtration membrane, such as for example, apart from PES, polymethyl methacrylate (PMMA), acrylonitrile based co- or ter-polymer.

The filtration membrane 113 with hollow fibres of the filtration device 110 furthermore preferably has an overall porosity comprised between 0 µm and 1 µm. Such a size of pores makes it possible to allow proteins and other drug molecules which are unsuitable to be transfused to pass through, while making it possible to conserve the compounds of interest of the haemorrhagic fluid, namely red blood cells, white blood cells and platelets.

In the proposed filtration device 110, the filtration membrane 113 has for example an overall filtration surface area greater than 0.04 m$^2$, for example comprised between 0.1 m$^2$ and 3 m$^2$, and preferably comprised between 0.2 m$^2$ and 0.6 m$^2$. More specifically, the filtration surface area is chosen so as to be at one and the same time sufficient to enable rapid filtration of the haemorrhagic fluid, typically in 5 minutes or less, but not too important to avoid too great protein adhesion and thus associated platelet loss. Preferably, the filtration device enabling filtration in less than 5 min for the treatment of a volume of 500 ml of haemorrhagic fluid is chosen.

The filtration device may according to a first example comprise a filtration membrane with hollow fibres arranged longitudinally in a cylindrical case, the filtration membrane having an average porosity of 0.6 µm, a filtration surface area of 0.2 m$^2$, said hollow fibres being formed from a mixture of polyester sulphone (PES) and polyvinyl pyrrolidone (PVP), having an inner diameter of 300 µm, an outer diameter of 470 µm, and a wall of 85 µm thickness.

According to a second example, the filtration device has the same characteristics as according to the first example but with a filtration surface area of 0.6 m$^2$.

According to a third example, the filtration device has the same characteristics as according to the first example but with a filtration surface area of 0.4 m$^2$.

The treatment unit 100 further comprises a treatment bag 140 which is fluidically connected to the filtration device 110 by a recirculation line 150.

More specifically, the treatment bag 140 has an inlet 140a and an outlet 140b fluidically connected by a recirculation line 150 to the outlet 111b and to the inlet 111a of the intake chamber 111 of the filtration device 110, respectively.

This arrangement notably enables circulation of the haemorrhagic fluid in the recirculation line 150 in a direction going from the outlet 140b of the treatment bag 140 to the inlet 140a of the treatment bag 140 through the intake chamber 111 of the filtration device 110.

Figure 5:
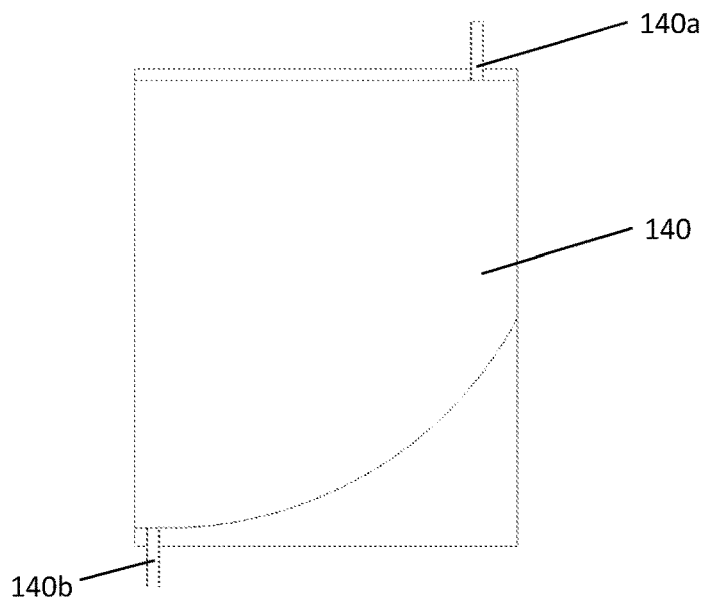
FIG. 5 is a schematic representation of a treatment bag for the treatment unit of a treatment system according to the invention.

The treatment bag 140 has a shape that is also provided to favour internal flow from the inlet 140a to the outlet 140b and to favour mixing of the treated blood fluid at the expense of an effect of sedimentation and of favoured circulation at the bottom of the bag. For example, as illustrated in FIG. 5, the treatment bag 140 has a substantially parallelepiped shape with the inlet 140a and the outlet 140b on either side of the treatment bag along a diagonal. Further preferably, the treatment bag further has an inner cavity having a tapering shape on the side of the outlet 140b, so as to make the fluid contained in the treatment bag 140 converge to the outlet 140b.

This treatment bag 140 has an active role in the treatment cycle of the haemorrhagic fluid. Firstly, as will be seen hereafter, it enables recirculation of the haemorrhagic fluid during a treatment cycle, that is to say several successive circulations in the filtration device 110, without variation in the circulation flow rate of the haemorrhagic fluid during said treatment cycle. It plays in effect the role of buffer zone which makes it possible to adsorb potential flow variations. The treatment bag 140 could also be used as zone for mixing the haemorrhagic fluid to be treated with a dilution fluid in order to favour the filtration and the elimination of soluble elements such as proteins and drug substances through the filtration device 110.

The treatment bag 140 may be equipped, without this being obligatory, with a separator device 141 being able to be actuated to separate the treatment bag 140 into a first treatment chamber 142 on the side of the inlet 140a of the treatment bag 140 and a second treatment chamber 143 on the side of the outlet 140b of the treatment bag 140. Such a separator device 141 may for example take the form of an electromechanical clamp being able to be actuated to form said first and second treatment chambers as a function of the sequencing of the treatment cycle.

The fluid drive means of the support unit 10 are provided to carry out mainly a circulation of the haemorrhagic fluid in the aforementioned direction—called direction of treatment—going from the outlet 140b of the treatment bag 140 to the inlet 140a of the treatment bag 140 through the intake chamber 111 of the filtration device 110. They may optionally also enable circulation in the opposite direction for certain specific phases of the treatment cycle as will be seen hereafter.

According to the exemplary embodiment of FIG. 2, a peristaltic pump 160 is provided in the recirculation line positioned in the recirculation line 150 between the outlet 140b of the treatment bag 140 and the inlet 111a of the intake chamber 111 of the filtration device 110. It makes it possible to circulate the haemorrhagic fluid in both directions of circulation specified above.

The treatment unit 100 furthermore comprises various ducts enabling the circulation of fluid within the treatment unit 100 itself with the circulation line 150 mentioned previously, but also to/from the other units of the treatment system.

Thus, the treatment unit 100 comprises an intake line 120 fluidically connected to the recirculation line 150 between the outlet 140b of the treatment bag 140 and the inlet 111a of the intake chamber 111 of the filtration device 110 making it possible to supply the treatment unit 110 with collected haemorrhagic fluid with a view to filtration through the filtration membrane 113 with hollow fibres of the filtration device 110 in order to remove from the haemorrhagic fluid a retentate comprising compounds not desired for autotransfusion. This intake line 120 is furthermore intended to be connected, removably, to the collection unit 200 described above.

Figure 7:
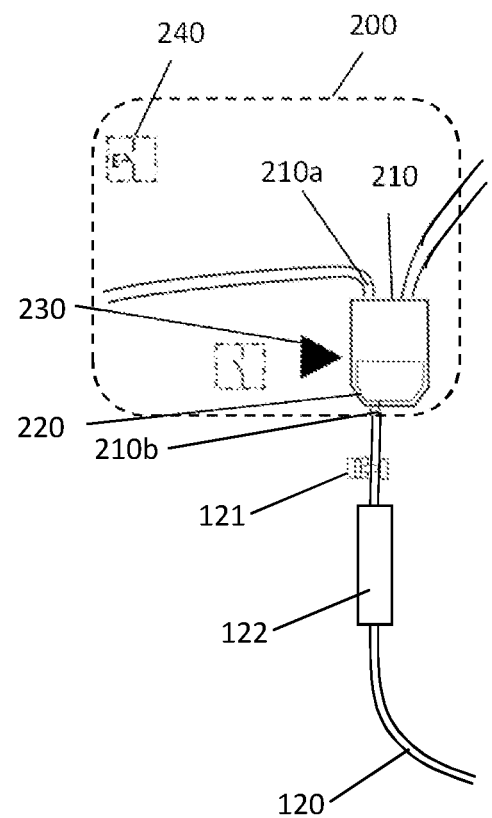
FIG. 7 is a schematic representation illustrating an exemplary positioning of an additional prefiltration device for the treatment system described.

As illustrated in FIG. 7, it may be provided to interpose in this intake line 120, on the side intended to be connected to the collection unit 200, an additional prefiltration device 122 making it possible to carry out an additional filtration before the actual filtration by the filtration device 110 of the treatment unit 100. The purpose of such an additional prefiltration device 122 is to retain the mass of coagulated substance, called coagulum, which is capable of forming at the outlet of the collection receptacle 210 despite the optional prefiltration device 220.

The additional prefiltration device 122 operates like a dynamic filter, that is to say that it must be able to operate with the flow rates imposed by the treatment unit, without deteriorating the treatment time performances. The additional prefiltration device 122 preferably has a level of filtration higher than the level of filtration of the optional prefiltration device 220 of the collection receptacle 210.

The additional prefiltration device 122 may for example have a level of filtration comprised between 40 µm and 200 µm, preferably comprised between 100 µm and 170 µm, further preferably of the order of 150 µm. The volume of retention of coagulum may be comprised between 5 ml and 100 ml, and preferably comprised between 20 ml and 50 ml.

Preferably, this additional prefiltration device 122 forms an integral part of the treatment unit 100. It may however also be envisaged that his additional prefiltration device is integrated in the collection unit 200, at the level of the outlet of the collection receptacle 210.

Preferably, this additional prefiltration device 122 is removably mounted in the treatment system, which makes it possible for example to be able to remove it and to clean it in the event of clogging.

The treatment unit 100 further comprises a transfusion line 170 also fluidically connected to the recirculation line 150 between the outlet 140b of the treatment bag 140 and the inlet 111a of the intake chamber 111 of the filtration device 110, and making it possible to recover the treated haemorrhagic fluid contained in said treatment bag 140. This transfusion line 170 is furthermore intended to be connected, removably, to the transfusion unit 400 described above.

Figure 3:
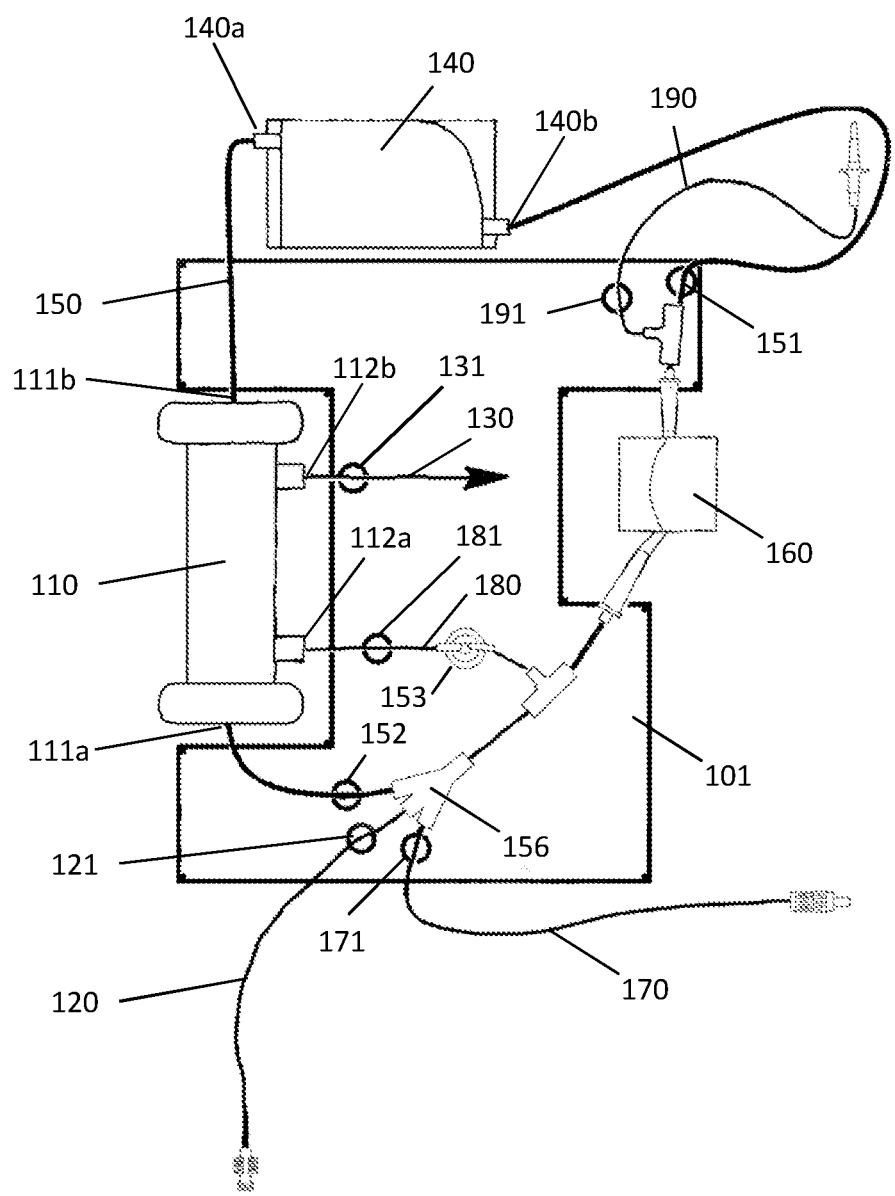
FIG. 3 is a representation of a treatment unit of a treatment system, according to a first embodiment of the first arrangement.
Figure 4:
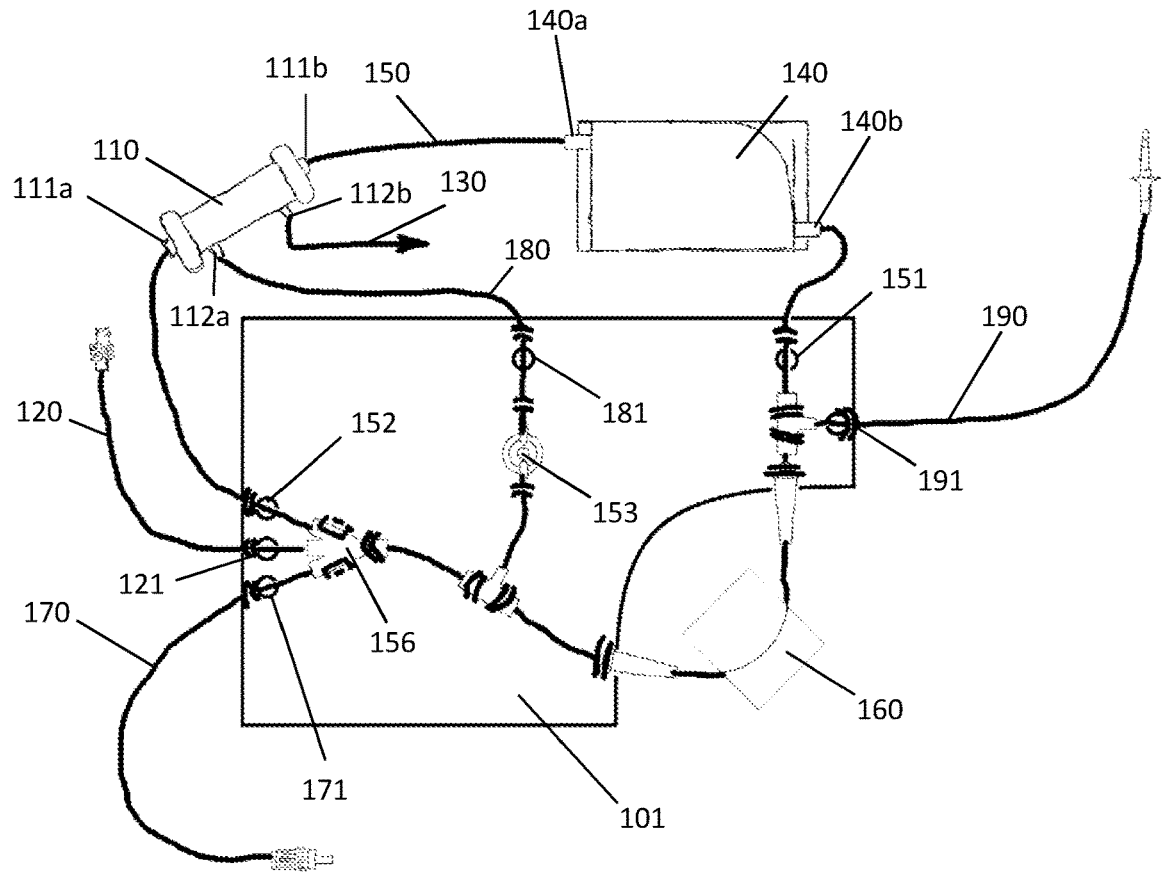
FIG. 4 is a representation of a treatment unit of a treatment system, according to a second embodiment of the first arrangement.

In a preferred manner, the intake line 120 and the transfusion line 170 are tapped at the same position on the recirculation line 150 as is illustrated in FIG. 2, with for example a multipath fluidic connector 156. A 3-way connector 156 as illustrated in FIGS. 2, 3, and 4 may thus be used, with an inlet path fluidically connected to the recirculation line 150 in the direction of the outlet 140b of the treatment bag 140, a first outlet path fluidically connected to the recirculation line 150 in the direction of the inlet 111a of the intake chamber 111 of the filtration device 110, a second outlet fluidically connected to the intake line 120, and a third outlet fluidically connected to the transfusion line 170.

Figure 6:
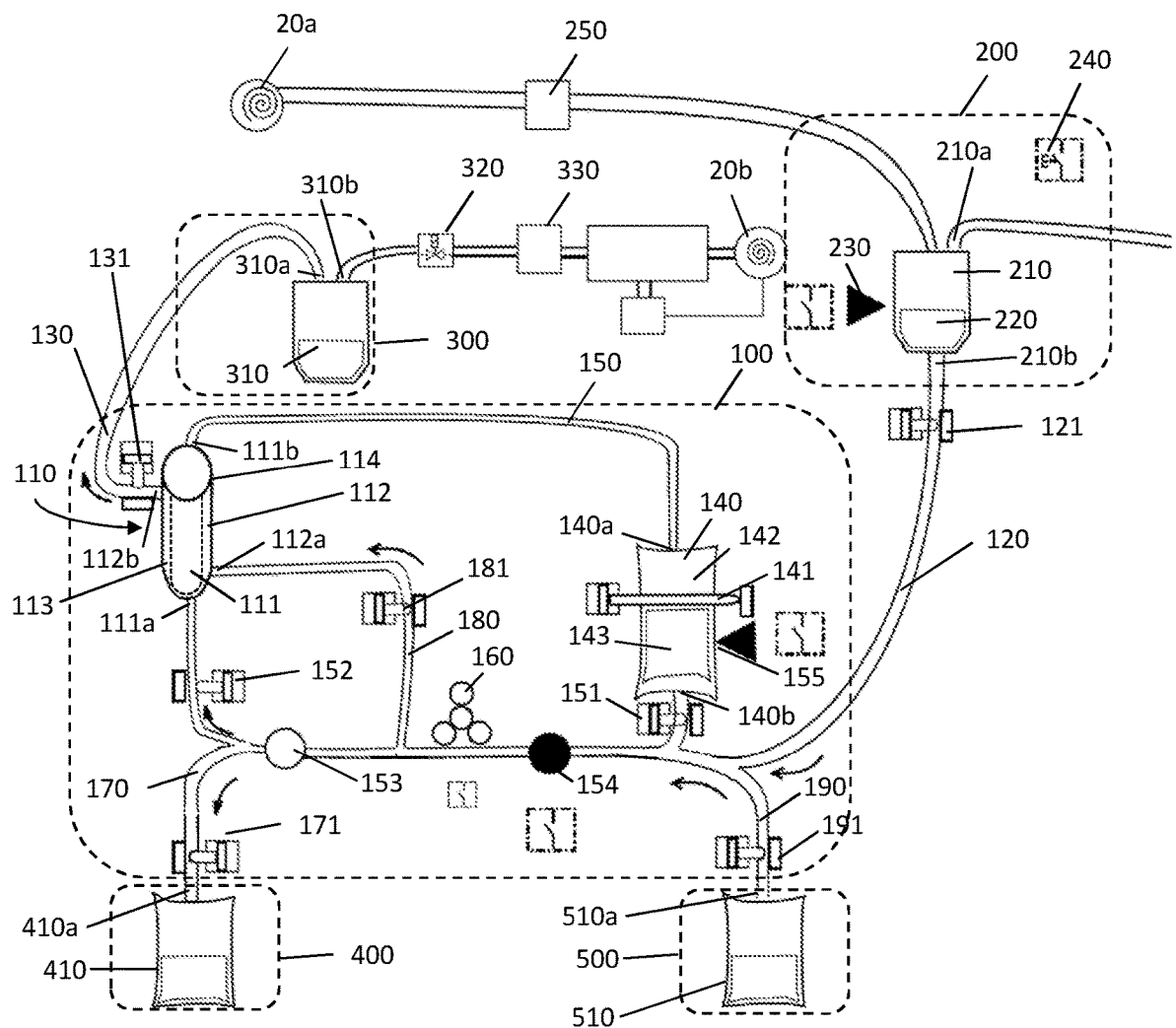
FIG. 6 is a schematic representation of a second arrangement of fluidic connections for the treatment system according to the invention.

As will be seen hereafter, and such as illustrated in FIG. 6, it could however be provided that the intake line is tapped upstream of the peristaltic pump 160, at the level of the outlet 140b of the treatment bag 140. In this case, the transfusion line is connected to the recirculation line by a standard 2-way fluidic connector. In this case, it is not necessary that the peristaltic pump 160 is suited to circulating the haemorrhagic fluid in both directions of circulation and it is sufficient to have a pump making it possible to circulate the haemorrhagic fluid along a single direction, namely the direction of treatment.

The treatment unit 100 furthermore comprises a discharge line 130 fluidically connected to the outlet 112b of the discharge chamber 112 of the filtration device 110 so as to discharge the filtrate having traversed the filtration membrane 113 with hollow fibres from the intake chamber 111. This discharge line 130 is furthermore intended to be connected, removably, to the discharge unit 130 described above.

When the recovery bag 310 is provided to be depressurised, by a vacuum system for example, this makes it possible to accelerate the filtration through the filtration membrane 113 of the filtration device 110 since said depressurisation is felt through the discharge line 130 into the discharge chamber 112.

The treatment unit 100 may furthermore comprise a cleaning line 180 fluidically connected to the inlet 112a of the discharge chamber 112 of the filtration device 110 to convey a cleaning fluid into said discharge chamber 112. It is to be noted that this cleaning line 180 is not obligatory in all the exemplary embodiments described.

The objective of this cleaning line 180 is to make it possible to convey a fluid into the discharge chamber 112 and to create a transmembrane counter-flow, that is to say a flow going in a direction opposite to the normal direction of flow through the filtration membrane 113 with hollow fibres of the filtration device 110 during filtration. This counter-flow through the filtration membrane 113 is very useful for disbonding all or part of the elements retained on the hollow fibres of the filtration membrane 113, and thus for regenerating the filtration capacities of the filtration membrane 113 notably in terms of efficiency and rapidity of filtration. The proposed counter-flow is also advantageous in that it enables cleaning of the filtration membrane in a simple and rapid manner, during a treatment cycle or between two treatment cycles.

A flow regulation member 181 may be provided arranged for flow regulation in the cleaning line 180 and another flow regulation member 131 arranged for flow regulation in the discharge line 130 in such a way as to be able to control the pressure of cleaning fluid in the discharge chamber 112.

The counter-flow may thus be created by obstructing the discharge line 130 at the level of the flow regulation member 131 and by injecting the cleaning fluid into the discharge chamber 112 from the cleaning line 180, the pressure created in the discharge chamber 112 by the injection of the cleaning fluid creating the required transmembrane counter-flow.

The cleaning fluid may be injected directly into the cleaning line 180 when this is required to create the counter-flow, an external source containing the cleaning fluid then being provided.

Whether the treatment unit 100 comprises a cleaning line 180 or not, a dilution line 190 making it possible to convey a dilution fluid into the treatment unit 100 may further be provided. The dilution line 190 is then preferably fluidically connected to the recirculation line 150 at a position between the outlet 140b of the treatment bag 140 and the inlet 111a of the intake chamber 111 of the filtration device 110. Preferably, the dilution line 190 is tapped upstream of the peristaltic pump 160.

This dilution line 190 is furthermore intended to be connected, removably, to a dilution unit 500 comprising a dilution receptacle 510 having an inlet/outlet orifice 510a intended to be coupled to the dilution line. The dilution receptacle 510 contains the dilution fluid that is intended to be injected into the treatment unit 100. This dilution fluid may be a crystalloid composition, preferably an isotonic solution compatible with erythrocytes, without carbohydrates or proteins, comprising for example sodium chloride, sodium lactate, and/or potassium chloride diluted in water to form an injectable preparation.

A flow regulation member 191 is preferably provided to enable flow regulation in the dilution line 190.

A device for controlling the dilution line 190 may be provided, said device being for example programmed to control the dilution fluid to convey into the treatment unit as a function of the haematocrit level measured by the haematocrit sensor, notably as a function of the haematocrit level of the haemorrhagic fluid to be treated, before treatment, as will be seen in detail hereafter.

The control device may for example be provided to actuate the flow regulation member 191.

In a preferred manner, the cleaning line 180 is fluidically connected to the recirculation line 150 at a position between the outlet 140b of the treatment bag 140 and the inlet 111a of the intake chamber 111 of the filtration device 110. When the treatment unit 100 comprises a dilution line 190, then the dilution fluid may be used to supply the cleaning line 180 and thus be used as cleaning fluid.

Preferably, another flow regulation member 151 is provided in the treatment unit 100 and arranged for flow regulation in the recirculation line 150 at the level of the outlet 140b of the treatment bag 140.

Yet another flow regulation member 152 is preferably provided so as to be able to carry out flow regulation in the recirculation line 150 at the level of the inlet 111a of the intake chamber 111 of the filtration device 110.

A flow regulation member 171 arranged for flow regulation in the transfusion line 170 may also be provided, thus making it possible to control the flow to transmit to the transfusion unit 400.

The exemplary embodiment shown in FIGS. 2 to 4 and 6 is a treatment system in which the treatment unit 100 requires a single peristaltic pump 160 for the circulation of fluids in the circuit, this peristaltic pump 160 being arranged in such a way as to circulate haemorrhagic fluid in the recirculation line 150 in a direction—designated direction of treatment—going from the outlet 140b of the treatment bag 140 to the inlet 140a of the treatment bag 140 through the intake chamber 111 of the filtration device 110.

Preferentially, this peristaltic pump 160 also makes it possible to circulate the flow in an opposite direction to the direction of treatment, that is to say going from the inlet 111a of the intake chamber 111 of the filtration device 110 to the outlet 140b of the treatment bag 140. This is particularly advantageous in the exemplary embodiment of FIG. 2 where the intake line 120 is tapped downstream of the peristaltic pump 160, that is to say at the level of the inlet 111a of the intake chamber 111 of the filtration device 110. Preferably, the peristaltic pump 160 is positioned in the recirculation line 150 between the outlet 140b of the treatment bag 140 and the inlet 111a of the intake chamber 111 of the filtration device 110 between the position where the dilution line 190 is fluidically connected to the recirculation line 150 and the position where the cleaning line 180 is fluidically connected to the recirculation line 150.

As a function of the envisaged operation of the treatment unit 100, the intake line 120 is tapped on the recirculation line 150 downstream of the peristaltic pump 160 as illustrated in FIG. 2, that is to say on the side of the inlet 112a of the intake chamber 112 of the filtration device, or is tapped on the recirculation line 150 upstream of the peristaltic pump 160, that is to say on the side of the outlet 140b of the treatment bag 140, as illustrated in FIG. 6.

In the case where the intake line 120 is tapped on the recirculation line 150 downstream of the peristaltic pump 160 as illustrated in FIG. 2, the haemorrhagic fluid will be, during the launch of a treatment cycle, transmitted preferably from the collection receptacle 210 to the treatment bag 140.

In the case where the intake line 120 is tapped on the recirculation line 150 upstream of the peristaltic pump 160, the haemorrhagic fluid will be, during the launch of a treatment cycle, transmitted preferably from the collection receptacle 210 directly through the filtration device 110. This has the advantage of not requiring a peristaltic pump 160 having to operate in both directions of circulation of the fluid.

As has been specified above, the treatment system preferably comprises sensors making it possible to monitor the evolution of the treatment during a specific treatment cycle.

A pressure sensor 153 within the circulation line 150 may in this respect be provided, notably arranged to detect pressure surges downstream of the peristaltic pump 160 in the direction of treatment.

A haematocrit sensor 154 may further be provided to measure the haematocrit level of the fluid circulating in the treatment unit 100. Preferably, the haematocrit sensor is arranged in such a way as to make it possible also to measure the haematocrit level of the fluid entering into the system, that is to say before any treatment.

By being positioned in a suitable manner, such as for example according to the arrangement illustrated in the figures, a single haematocrit sensor 154 may make it possible to measure the haematocrit level of the haemorrhagic fluid before treatment, during treatment, and after having been treated.

Optionally, several haematocrit sensors are positioned at different points of the treatment system. It could be possible for example to provide specific positionings of different haematocrit sensors to be able to measure the haematocrit level of the haemorrhagic fluid before treatment, during treatment, and after having been treated.

Such a haematocrit sensor 154 may for example be an optic sensor formed of an assembly of infrared emitting diodes and receivers.

A weighing system 155 may also be provided, such as a force sensor forming weight indicator, arranged to measure the quantity of fluid present in the treatment bag 140. This weighing system 155 is going to make it possible to give information for controlling the treatment cycle, making it possible for example to trigger a transfer of the treated haemorrhagic fluid to the transfusion unit 400 when the target parameters, notably in terms of haematocrit level, are reached.

The treatment unit 100 being a consumable, intended to be replaced for each new patient notably, it is preferable that its handling is simple and easy. Since this treatment unit 100 comprises a certain number of different components and tubing forming the fluid circulation lines, a template 101 may be provided which notably enables a fixation of the intake line 120, the discharge line 130, the recirculation line 150, the transfusion line 170, as well as the cleaning line 180 and/or the dilution line 190 if needs be. The filtration device 110 and the treatment bag 140 are integral parts of the treatment unit 100 and are thus connected beforehand to the corresponding tubing and to the template 101. The treatment unit 100 thus proposed may thus be proposed as a consumable in kit form, to be replaced according to needs.

The template 101 is also provided to enable an easy putting in place on the support unit 10 and has in this respect a fool proof device shape making it possible to couple the treatment unit 100 to the support unit 10 according to a unique positioning.

Furthermore, the filtration device 110 of the treatment unit 100 is intended to be coupled to the support unit 10 such that the hollow fibres of the filtration membrane 113 extend along a direction not comprised in the horizontal support plane defined by the support unit 10, that is to say that the filtration device 110 is inclined with respect to the horizontal support plane.

It is to be noted that this horizontal support plane corresponds to the transversal plane of the support unit 10, which is parallel to the horizontal plane when the support unit 10 is laid on the ground.

The example of FIG. 3 illustrates a treatment unit 100 having a template 101 provided for a vertical placement of the template 101, that is to say that the template 101 is fixed in a plane different to the horizontal support plane of the support unit 10, for example an inclined plane, and preferably a vertical plane (that is to say perpendicular to the horizontal support plane). According to this embodiment, the filtration device 110 may also be fixed to the template 101 since the putting in place of the template 101 will necessarily lead to an inclined arrangement of the filtration device 110.

The example of FIG. 4 illustrates a treatment unit 100 having a template 101 provided for a horizontal emplacement of the template 101, that is to say that the template 101 is fixed in a plane parallel to the horizontal support plane of the support unit 10. According to this embodiment, the filtration device 110 is not fixed to the template 101 and will have to be fixed to the support unit 10 in an independent manner to be arranged inclined with respect to the horizontal support plane.

As illustrated in FIGS. 3 and 4, the flow regulation members that have been described previously may take the form of orifices arranged opposite the tubing forming the fluid circulation lines where the flow must be controlled. Regulation valves are then provided, for example solenoid valves operating with electromagnets, arranged to abut against the tubing through the orifices in order to control the section of the tubing and thus the flow of fluid being able to pass therethrough. In a preferred manner, these regulation valves are directly mounted on the support unit 10 and may thus be used for different successive treatment units 100.

The putting in place of the treatment unit 100 including a template 101 is very simple. It suffices in effect to position the template 101 in the housing provided for this purpose on the support. When the flow regulation members are orifices intended to cooperate with solenoid valves of the support unit 101, the placing opposite is automatic thanks to the fool proof device shape of the template 101. Once the template 101 is in place on the support unit 10, it is advisable to connect the intake line 120 to the intake unit 200, the discharge line 130 to the discharge unit 300, the transfusion line 170 to the transfusion unit 400, and optionally the dilution line 190 to the dilution unit 500. It is to be noted that some of the units could be preconnected to their respective lines, that is to say already be connected to the treatment unit 100 before being put in place on the support unit 10. For example the transfusion unit 400 is preferably preconnected to the transfusion line 170, and the discharge unit 300 may also be preconnected to the discharge line 130. When the filtration device 110 and/or the treatment bag 140 are not fixed to the template 101, it is advisable to fix them on the support unit 10.

The treatment flow rate is chosen sufficiently high to apply an important shear force that limits protein and platelet adhesion at the level of the filtration device, without however being too important, which would create undesired haemolysis. The flow rates chosen are very much greater, generally from 5 to 10 times greater, than the flow rates generally recommended for a filtration device using a filtration membrane with hollow fibres. It has been observed in fact that the filtration results are very positive in terms of cell concentration, and the high circulation flow rates are not a hindrance since the treatment system is not directly connected to the patient, but uniquely indirectly via the collection unit 200 on the one hand and the transfusion unit 400 on the other hand when the latter are connected to the patient. In practice, as indicated above, the treatment unit 100 preferably operates with a flow rate comprised between 10 ml/min and 4000 ml/min, and preferably between 100 ml/min to 2100 ml/min, for example at 1400 ml/min or 700 ml/min.

The application of a controlled vacuum between 0 to −100 kPa at the level of the recovery unit 300 through the discharge line 130 makes it possible to improve the speed of filtration and to maintain it constant. In addition, during a reversal of the transmembrane flows (notably during counter-flow cleaning) a de-priming of the filtration may be observed if a depressurisation is not applied continuously, thus making the continuation of the blood treatment impossible.

Apart from the aforementioned advantages in terms of cleaning for extending the lifetime and the filtering efficiency of the filtration device 110, the passage of the dilution fluid for rinsing the filtration membrane 113 with hollow fibres between two treatment cycles also contributes to platelet recovery.

The treatment system proposed for the treatment of haemorrhagic fluid with a view to autotransfusion is simple to use and enables rapid treatment of haemorrhagic fluid taken from the patient with qualitative performances better than existing devices. All or part of the performances indicated below can in fact be reached with the proposed treatment device:

- Average yield of platelets greater than or equal to 40%, or even greater than or equal to 50%, or even greater than or equal to 60%, and even greater than or equal to 70%;
- Average yield of red blood cells (RBC) greater than or equal to 80%, or even greater than or equal to 90%, and even greater than or equal to 95%, or even of the order of 99%;
- Average yield of white blood cells (WBC) greater than or equal to 80%, or even greater than or equal to 90%, and even greater than or equal to 95%, or even of the order of 97%;
- Reduced haemolysis, or even zero or close to zero haemolysis. The target haemolysis will be able to be for example less than 1%, preferably less than 0.8%;
- Elimination of free haemoglobin greater than or equal to 95%, or even greater than or equal to 98%;
- Residual concentration of heparin in the transfusion bag after treatment less than or equal to 0.5 UI/m$^1$;
- Treatment time for a volume of 500 ml of haemorrhagic fluid to make it suitable for transfusion which is less than or equal to 10 min, preferably less than or equal to 8 min, preferably less than or equal to 6 min, and in an optimal manner of the order of or less than or equal to 5 min.

It is to be noted that the level of qualitative performances indicated above has to be modulated as a function of the operating conditions.

For example, if treatment must be carried out very rapidly, it is possible that the performances are a little diminished.

In the same way, if it is decided to concentrate the treated haemorrhagic fluid several times, for example during a triple concentration, in order to be certain of eliminating compounds not desired for autotransfusion, such as products not desired for transfusion, of heparin type, it is possible that some of the performances are diminished, without that however reducing the overall performance of the proposed treatment system compared to existing systems.

Operation of the System for Treating Haemorrhagic Fluid with a View to Autotransfusion An exemplary operation of the proposed treatment system is described below, according to a standard mode, and is in no way limiting. The proposed treatment system could in fact be used in standard mode according to different specific phases, adapted as a function of the need of the surgical intervention or the transfusion need. The operation of the proposed treatment system may also be suited to particular operational situations, for example in an emergency when a transfusion is necessary even if the treatment is not totally finished, or when the volume of haemorrhagic fluid to be treated is not optimal for the standard treatment cycle.

The exemplary operation below is presented with reference to the first arrangement of the treatment unit 100 such as illustrated in FIGS. 2 to 4. According to this arrangement, it is possible to dilute the haemorrhagic fluid before launching the concentration by passage through the filtration device. The volume of dilution fluid used may be fixed beforehand or modulated as a function of the initial concentration of the collected blood, that is to say as a function of the haematocrit level of the haemorrhagic fluid to be treated. The volume of rinsing fluid used for the dilution may be 200 ml for a 500 ml bolus of haemorrhagic fluid, but this volume of rinsing fluid could be much higher, for example of the order of 18 litres (depending on the initial concentration of anticoagulant in the haemorrhagic fluid). This dilution volume may be added at the start of treatment or per bolus from several m$^1$ to several hundreds of m$^1$ during treatment, after a first concentration or not of the volume of haemorrhagic fluid.

In an exemplary operation according to the second arrangement of the treatment unit 100 such as illustrated in FIG. 6, the haemorrhagic fluid entering into the treatment unit is concentrated, in passing through the filtration device, before the addition of the rinsing fluid.

Indeed, the haemorrhagic fluid directly passes through the filtration device 113 during its transfer from the collection unit 200 to the treatment bag 140. The advantage of a filtration before addition of dilution fluid is direct elimination of soluble elements during transfer to the treatment bag. In this case, the fact of being able to unclog the filtration device is particularly advantageous since it will have a tendency to foul more rapidly.

A. Phase of Preparation of the Treatment System

The phase of preparation of the proposed treatment system will firstly be described, comprising a phase of installation of the components of the treatment system then a phase of initialisation and of testing of this treatment system.

All the clamps formed by the solenoid valves for the regulation of the flows of fluid are in open position.

The collection unit 200, the recovery unit 300, the transfusion unit 400 and the dilution unit 500 are installed on the support unit 10.

Next the treatment unit 100 is installed on the support unit 10. The clamp of the regulation valve 121 of the intake line 120 and that of the regulation valve 191 of the dilution line 190 are closed.

The different units are finally connected by means of the piping of the corresponding fluid circulation lines, and associated connectors, these connectors being for example of "Luer Lock" type.

The collection unit 200 and the recovery unit 300 are connected to wall vacuum sockets (20a; 20b). A source of heparinised crystalloid solution may furthermore be connected to the inlet 210a of the collection receptacle 210.

Once all the elements have been connected to the support unit 10, the treatment system may be started (electrical supply) and a phase of initialisation and of testing of the treatment system is launched, controlled by the central unit of the support unit 10.

In this test phase, it is verified that all the units are correctly connected to the support unit 10 and to each other. Optical contacts placed at the level of the support unit 10 may for example also be used, notably so that the central unit obtains this type of information.

In initialisation, a control of the central unit controls the clamps of the different lines so that the regulation valves are all in closed position.

The vacuum sources are now supplied and the treatment system is operational to launch a treatment cycle.

B. Preparatory Phase of the Circuit of the Treatment Unit Before the First Treatment Cycle Before launching an actual treatment cycle, in a preferred but optional manner a preparatory phase of the treatment cycle may be carried out which makes it possible to improve the efficiency of the actual treatment cycle.

This preparatory phase may be carried out ahead of the surgical intervention, but it is preferred to do it during the surgical intervention, as soon as bleeding is observed and when an autotransfusion is envisaged.

A priming of the collection unit 200 is firstly carried out by filling the collection receptacle 210 by aspiration of heparinised crystalloid solution until a certain volume is obtained in said collection receptacle 210. This aspiration may for example be carried out by application of a vacuum in the collection receptacle 210 of the order of 300 mbars. The collection receptacle 210 is filled with for example 200 ml of heparinised crystalloid solution. This priming of the collection unit with heparinised crystalloid solution makes it possible to moisten the collection unit 200 which is going to facilitate the prefiltration therewithin, in terms of speed of filtration notably. Further, this makes it possible to heparinise the materials and thus limit the phenomenon of coagulation.

A priming is then carried out of the recirculation line of the treatment unit 100 in which the actual treatment is conducted. This priming may notably start when bleeding is active. To do so, the depressurisation of the recovery unit 300 is activated, for example a vacuum is applied through the filtration device 110 while activating the valve 320, while the regulation valve 121 of the intake line 120 and the regulation valve 191 of the dilution line 190 being closed and all the other clamps open. The clamps of the regulation valve 181 of the cleaning line 180, the regulation valve 151 of the recirculation line 150, the regulation valve 171 of the transfusion line 170 are next closed, and the clamp of the regulation valve 191 of the dilution line 190 is opened. The peristaltic pump 160 is started up and the recirculation line 150 fills up with dilution fluid from the dilution unit 500. The air present in the circuit is expelled via the discharge line 130 and dilution fluid progressively fills the different empty chambers with the elements of the treatment unit 100, in particular the filtration device 110 and the treatment bag 140.

After a time delay for filling the recirculation line, if needs be a priming of the cleaning line 180 is carried out. In this respect, while the depressurisation of the recovery unit 300 is still active, with for example a vacuum applied through the recovery unit 300, the clamp of the regulation valve 181 of the cleaning line 180 is opened then the clamps of the regulation valve 152 of the recirculation line 150 and the regulation valve 151 of the recirculation line 150 are closed. The dilution fluid then circulates through the cleaning line 180 into the discharge chamber 112 of the filtration device 110 then through the hollow fibres of the filtration membrane 113 in counter-flow.

This priming of the recirculation line and the cleaning line 180 of the treatment unit 100 progressively fills the treatment bag 140 with dilution fluid.

Preferentially, these priming phases are continued until a certain volume of dilution fluid is present in the treatment bag 140, this fluid will serve to dilute/wash the haemorrhagic fluid to be treated. Preferably, the clamp of the regulation valve 131 of the discharge line 130 is closed, and the vacuum valve 320 is also closed, to fill the treatment bag 140 more quickly with the dilution fluid. In the treatment bag, filling with dilution fluid continues to reach a volume— designated washing volume—useful for the first treatment cycle. A washing volume of 200 ml is for example used when it is wished to treat a bolus of haemorrhagic fluid of around 500 ml. As will be seen hereafter, this washing volume will be able to vary, notably as a function of the haematocrit level of the haemorrhagic fluid to be treated. When the weight indicator 155 of the treatment bag 144 detects that the wash weight (=volume) is reached, the pump 160 is stopped.

It could also be envisaged not to fill the treatment bag 140 and quite the opposite empty it via the discharge unit 300, after the priming phase. In this case, the dilution of the bolus of haemorrhagic fluid will be carried out directly during the treatment phase, when the haemorrhagic fluid is injected into the circuit of the treatment unit 100.

The treatment unit 100 is thus ready to receive a first bolus of haemorrhagic fluid to be treated and to carry out the first treatment cycle. While waiting for the collection receptacle 210 to contain a sufficient quantity of haemorrhagic fluid for the first treatment cycle (for example around 500 ml), the clamps of the regulation valve 181 of the cleaning line 180 and the regulation valve 191 of the dilution line 190 are closed, such that all the clamps are closed.

It is the weight indicator 230 of the collection receptacle 210 that will trigger the launch of the treatment when the quantity of haemorrhagic fluid to be treated is sufficient.

It is to be noted that the opening/closing order of the different clamps is chosen to enable the pump to operate continuously and thus to have continuous circulation of fluids in the treatment unit 100.

C. Phase of Treatment of the Haemorrhagic Fluid

In the overall autotransfusion process, there are three successive steps independent of each other:

E1. Collection of the haemorrhagic fluid, where an intervention on the patient is necessary. The haemorrhagic fluid is in fact collected from the patient and transferred into the collection receptacle 210 of the collection unit 200.

E2. Treatment of the collected haemorrhagic fluid, which is done without any link with the patient. This treatment step is carried out with the proposed treatment system, notably in the treatment unit 100.

E3. Transfusion of the treated haemorrhagic fluid, where an intervention on the patient is necessary. The haemorrhagic fluid that has been treated by the treatment unit 100, then transferred into the transfusion bag 410 of the transfusion unit 400, may be transfused into the patient. To do so, it is preferable to disconnect the transfusion bag 410 from the treatment system to connect it to the patient.

The description that follows specifies step E2 of treatment of haemorrhagic fluid collected beforehand from a patient during step E1. Whether there is a preparatory phase of the circuit of the treatment unit 100 as described above or not, the first treatment cycle will start when the volume of haemorrhagic fluid in the collection receptacle 210 will have reached a threshold, this threshold preferentially corresponding to the volume of the bolus that it is wished to treat in a treatment cycle, this bolus of haemorrhagic fluid being for example chosen of the order of 500 ml.

Thus, to treat volumes of haemorrhagic fluid greater than the volume fixed for a bolus to be treated during a treatment cycle, it will be advisable to carry out several successive treatment cycles.

It is to be noted that the treatment cycle could, in certain particular cases, be carried out with a volume of haemorrhagic fluid less than the volume fixed for the treatment bolus, such as for example at the end of treatment where there remains less haemorrhagic fluid to be treated, at the end of bleeding, or at any opportune moment chosen by the practitioner. It should however be noted that it will be necessary all the same that the volume of haemorrhagic fluid to be treated is greater, preferably at least two times greater, than the dead volume of the treatment circuit (VmTT), that is to say the volume comprised between the outlet 140b of the treatment bag 140 and the inlet 140a of the treatment bag 140, that is to say the volume of the recirculation line 150 and the inside of the filtration device 113.

According to another embodiment, the volume of haemorrhagic fluid to be treated is not fixed beforehand but is variable.

In this case, the volume of the bolus of haemorrhagic fluid to be treated is notably calculated as a function of the quantity of red blood cells that it is wished to obtain in the volume of haemorrhagic fluid to re-transfuse.

For example, the volume of the bolus of haemorrhagic fluid to be treated may be calculated as a function of the haematocrit level of the haemorrhagic fluid to be treated and the target haematocrit level that it is wished to obtain for a volume of haemorrhagic fluid to re-transfuse.

The haematocrit level of the haemorrhagic fluid to be treated may in this case be measured before treatment, with a haematocrit sensor of the treatment system for example.

As already indicated, the treatment cycle is going to be able to be launched automatically as soon as the weight indicator 230 of the collection receptacle 210 will have measured the target quantity of the bolus. This bolus may for example be equal to 500 ml of haemorrhagic fluid. This bolus will be able to be mixed with dilution fluid stored in the treatment bag 140 (for example a volume of 200 ml) during the phase of pre-treatment and priming of the treatment unit 100. In the event where the dilution volume is not present in the treatment bag 140, for example when no pre-treatment phase will have been launched or when the treatment starts with a filtration phase in the filtration device 113, it will be possible to introduce directly the volume of dilution fluid required into the recirculation line 150 from the dilution unit 500, To mix the haemorrhagic fluid of the collection receptacle 210 with the dilution fluid present in the treatment chamber 140, it is appropriate firstly to fill the treatment bag 140 with said haemorrhagic fluid. To do so, the clamps of the regulation valve 121 of the intake line 120 and the regulation valve 151 of the recirculation line 150 are opened and the peristaltic pump 160 is started up in reversed rotation, that is to say to drive the haemorrhagic fluid in the opposite direction to the direction of treatment, to the outlet 140b of the treatment chamber 140. When the weight indicator 155 of the treatment bag 140 detects that the target treatment volume has been reached, the peristaltic pump 160 is stopped. It is to be noted that this mixing step could be carried out by firstly injecting the haemorrhagic fluid into the treatment bag 140 or by carrying out beforehand a filtration and concentration then by injecting the dilution fluid into this same treatment bag 140 if it is not already present.

The actual phase of treatment of the haemorrhagic fluid may next start, with a filtration and concentration until the target haematocrit level is obtained. In general, the sought after haematocrit level is of the order of 45%+/−5%, but it could be of the order of 50%+/−5%, 55%+/−5%, or even at the most of 60%+/−5%. For this phase, the clamp of the regulation valve 121 of the intake line 120 is thus going to be closed then the clamps of the regulation valve 152 of the recirculation line 150 and the regulation valve 131 of the discharge line 130 opened; the electric control valve 320 is also actuated to impose a vacuum on the discharge chamber 112 through the recovery unit 300. The peristaltic pump 160 is then actuated in the direction of treatment, such that the fluid contained in the treatment bag 140 circulates from the outlet 140b to the inlet 111a of the intake chamber 111 of the filtration device 110, then from the outlet 111b of the intake chamber 111 of the filtration device 110 to the inlet 140a of the treatment bag 140.

On passing through the filtration device 110, the haemorrhagic fluid to be treated is filtered by the filtration membrane 113 with hollow fibres and is progressively stripped of compounds not desired for autotransfusion (such as proteins and other drug molecules which are unsuited to be transfused), these passing through the filtration membrane 113 up to the discharge chamber 112 before being sucked up by the depressurisation of the recovery unit 300 through the discharge line 130. The recirculation of the haemorrhagic fluid in the recirculation line 150 through successively the filtration device 110 and the treatment bag 140 is carried out until the target haematocrit level is obtained, this haematocrit level being for example detected at the level of the haematocrit sensor 154. The stoppage of the treatment may also be controlled by calculating the theoretical haematocrit level of the haemorrhagic fluid present in the treatment bag 140 as a function of the weight of the treatment bag (measured for example with the weighing system 155) and from the input haematocrit level of the haemorrhagic fluid, that is to say the haematocrit level of the haemorrhagic fluid before treatment and the volume of haemorrhagic fluid to be treated.

This is referred to as concentration by filtration, that is to say that the haemorrhagic fluid is filtered until reaching a certain concentration of red blood cells corresponding to the target haematocrit level for the transfusion, while at the same time removing from the haemorrhagic fluid a filtrate comprising compounds not desired for transfusion, such as for example heparin. A concentration of the haemorrhagic fluid thus comprises in general successively several filtrations through the filtration device 110 and re-circulations through the treatment bag 140.

Once the target haematocrit level has been reached and once the volume of concentrate (corresponding to the treated haemorrhagic fluid) in the treatment bag 140 is sufficient (for example greater than 100 ml), it may be envisaged to transfer this concentrate to the transfusion bag 410 of the transfusion unit 400.

Preferably but in a non-obligatory manner, a rinsing of the recirculation line 150 and the filtration membrane 113 of the filtration device 110 is carried out. More specifically, it is envisaged to rinse the dead volume of the filtration circuit (VmCF) which corresponds to the volume of circuit comprised between the transfusion unit 400 and the treatment bag 140 passing through the filtration device 110. In this respect, the clamps of the regulation valve 151 of the recirculation line 150 and the regulation valve 131 of the discharge line 130 are closed and the clamp of the regulation valve 191 of the dilution line 190 is opened. The peristaltic pump 160 rebegins its operation in the direction of treatment to convey the dilution fluid from the dilution unit 500 in the direction of the filtration device 110, this dilution fluid being injected in order to push the column of blood from the VmCF, the fluids next being able to be stored in the treatment bag 140.

A rinsing of the intake line 120 may also be carried out, in a concomitant manner or not to the rinsing of the recirculation line 150 and the filtration membrane 113, and does so to avoid any coagulation within this intake line 120. Preferably, the rinsing of this intake line 120 is carried out between the different treatment cycles, and the dilution fluid of the dilution unit 500 or the fluid present in the treatment bag 140 may for example be used.

It is possible to provide an optical sensor placed at the level of the inlet 140a of the treatment bag 140 which makes it possible to detect the nature of the fluid arriving at the level of the inlet 140a. If such a sensor is used, it is then possible of stop the pump 160 to stop the rinsing phase as soon as the optical sensor detects the presence of dilution fluid. Such an optical sensor makes it possible to control the stoppage of the pump 160 before washing fluid comes into the treatment bag.

For this rinsing phase, it is desirable that the treatment bag 140 integrates the separator device 141 which makes it possible to confine the concentrate in the treatment chamber 142, in the lower part of the treatment bag 140 on the side of the outlet 140b of the treatment bag 140. The other treatment chamber 141 formed by the separator device 141 in the upper part of the treatment bag 140 on the side of the inlet 140a of the treatment bag 140 makes it possible to recover the fluid contained in the circuit and pushed by the dilution fluid in the rinsing phase.

It is to be noted that it is also possible to carry out several successive phases of concentration of the same bolus of haemorrhagic fluid to be treated. This notably makes it possible to even better eliminate compounds not desired for autotransfusion, such as products undesirable for transfusion, of heparin type. Preferably, a triple concentration is carried out for a same bolus of haemorrhagic fluid to be treated.

In a favoured manner, when several successive concentrations are carried out, once the bolus of haemorrhagic fluid to be treated has reached the target haematocrit level after a phase of concentration, the treated haemorrhagic fluid is again going to be diluted to eliminate impurities during a new concentration.

When transfer is desired, after optional rinsing or directly after the phase of filtration and concentration, and/or after several concentration phases, it is advisable to close the clamps of the regulation valve 152 of the recirculation line 150 and the regulation valve 191 of the dilution line 190 (if this is not already the case) and open the clamps of the regulation valve 171 of the transfusion line 170 and the regulation valve 151 of the recirculation line 150 (if this is not already the case). The peristaltic pump 160 is then started in the direction of treatment and the concentrate is thus transferred from the treatment bag 140 into the transfusion bag 410 of the transfusion unit 400.

It is to be noted that the volume of concentrate present in the treatment chamber 140 could be conserved and thus not transferred immediately to the transfusion unit 400. The concentrate will then be cumulated with the concentrate resulting from a subsequent treatment cycle, that is to say with another bolus.

Once the concentrate has been transferred wholly or partially to the transfusion unit 400, the treatment cycle is terminated and another treatment cycle may be triggered with another bolus of haemorrhagic fluid.

Step E3 of transfusion of the treated haemorrhagic fluid to the patient may be carried out, by disconnecting notably the transfusion bag 410 from the treatment system, and by connecting it to the patient. If a transfusion is not necessary immediately, the transfusion bag 410 may also be stored, a new transfusion bag 410 being connected to the treatment system, in order to be able to recover the newly treated haemorrhagic fluid.

As indicated above, the treatment of the haemorrhagic fluid may be optimised by controlling the volume of haemorrhagic fluid to be treated.

This is notably advantageous for ensuring that the bolus of haemorrhagic fluid to be treated makes it possible to obtain the quantity of red blood cells necessary to reach the target haematocrit level after treatment.

In the case where the treatment consists in several successive concentrations and where a dilution step is provided before each concentration, this control of the volume of haemorrhagic fluid to be treated is also advantageous to adapt and determine the optimum volume of dilution fluid so that the treatment as a whole is the most efficient possible, notably so that it is carried out as quickly as possible while limiting, notably, the phenomenon of haemolysis.

Thus, the starting volume contained in the collection unit 200 and transferred into the treatment unit 100 may be calculated by a programme, the objective of which is to obtain a quantity of erythrocyte in the treatment bag whatever the initial concentration of red blood cells of the haemorrhagic fluid to be treated. This quantity of erythrocyte corresponds to the minimum fixed to enable transfusion of a certain volume of haemorrhagic fluid.

For example, when it is wished to obtain a volume of 300 ml of concentrate with a haematocrit level of 45%, it is necessary to use a volume of haemorrhagic fluid to be treated which will make it possible to obtain at least 135 ml of red blood cells after treatment. The volume of haemorrhagic fluid to be treated is thus calculated to obtain this minimum quantity of red blood cells after filtration, here 135 ml.

Apart from taking into account the target haematocrit level, the optimum volume of haemorrhagic fluid to be treated may thus be determined as a function of the measured haematocrit level of said haemorrhagic fluid to be treated.

According to a first embodiment, the volume of haemorrhagic fluid to be treated is directly controlled as a function of a measurement of the haematocrit level of this haemorrhagic fluid. Thus, a volume is fixed for the bolus of haemorrhagic fluid to be treated which is greater than or equal to the theoretical volume needed to obtain the desired quantity of red blood cells in the treated haemorrhagic fluid.

To compensate for potential errors in measurement of the haematocrit level of the haemorrhagic fluid to be treated and/or to compensate for possible losses of red blood cells during the treatment process, it is possible to use a volume for the bolus of haemorrhagic fluid to be treated which is greater than the theoretical volume, for example greater by 5%, 10%, 15% or 20%.

Preferably, the volume used for the bolus of haemorrhagic fluid to be treated is not greater than more than 50% of the theoretical volume.

According to a second embodiment, the volume for the bolus of haemorrhagic fluid to be treated is calculated as a function of the volume $V_T$ of haemorrhagic fluid having been transferred into the treatment bag 140 before launching the treatment as such. It should be recalled that depending on the arrangement of the treatment unit, the haemorrhagic fluid may be directly transferred into the treatment bag 140 without passing through the filtration device 110 (example illustrated in FIGS. 2 to 4), or it may be transferred into the treatment bag 140 while passing at least once through the filtration device 110 (example illustrated in FIG. 6).

Let us take the case of a treatment system which makes the haemorrhagic fluid to be treated enter from the collection unit 200 into the treatment unit at a certain collection flow rate $D_P$. The filtration flow rate Df through the filtration device of the treatment unit is also known.

According to a first example of this second embodiment, the treatment system can calculate a collection time in the collection unit 200.

To obtain Xe m$^1$ (=ET) of red blood cells in the treatment bag, of an incoming haemorrhagic fluid with a haematocrit level of $Y_E$%, it is necessary to have Zp (=$V_P$) m$^1$ of haemorrhagic fluid to be treated to collect from the collection unit 200: Zp=Xe/Ye Thus, for a collection flow rate $D_P$, the time to obtain this quantity of red blood cells in the treatment bag will be:

$$Tp = Zp/D_P \tag{F1}$$

According to a second example of this second embodiment, the treatment system is provided to control the volume Za (=$V_T$) of blood taken into the treatment bag. The collection flow rate $D_P$ and the filtration flow rate Df are known parameters of the treatment system (for example, a $D_P$ comprised between 900 ml/min and 1200 ml/min, and a Df comprised between 150 ml/min and 500 ml/min), the input haematocrit level $Y_E$ of the haemorrhagic fluid to be treated is measured, this haematocrit level being variable.

The treatment system may be programmed to estimate the haematocrit level at the outlet of the filtration module Ys.

If one has a collection flow rate $D_P$ of haemorrhagic fluid at concentration $Y_E$ taken in at the inlet of the filtration device 110 of which the filtration flow rate is Df, one will have a flow rate $D_T$ of filtered haemorrhagic fluid at the outlet of the filtration device at concentration Ys. Thus $D_T = D_P - Df$.

After filtration, one will have the transferred volume=$V_T$, the collected volume $V_P$ and the filtrate volume $V_F$ such that $V_T = V_P - V_F$.

The input haematocrit level of the haemorrhagic fluid to be treated is given by $Y_E$=Qe htie/$V_P$, where Qe is the quantity of erythrocyte present in the volume of the haemorrhagic fluid to be treated.

The outlet haematocrit level of the filtered haemorrhagic fluid is given by Ys=Qs htie/$V_T$, where Qs is the quantity of erythrocyte present in the volume of filtered haemorrhagic fluid. Thus, one has: Ys=Qs htie/($V_P - V_f$)

Considering Qs htie=Qe htie, one obtains: Ys=Qe htie/($V_P - V_f$)

Thus, since Qe htie=$Y_E$*$V_P$, one deduces therefrom: Ys=$Y_E$*$V_P$/($V_P - V_f$)

i.e. again: $Ys = Y_E \cdot D_P/(D_P - Df)$ (F2)

The treatment system measuring the volume in the treatment bag, for example by means of the corresponding weighing system, this treatment bag is thus going to be filled until the quantity of erythrocyte therein has reached its value target: Qte htie in the treatment bag=$V_T$ target*Ys.

And thus: $V_T$ target=$Qshtie/Ys$ (F3)

Thus from the collection unit 200, a certain quantity of haemorrhagic fluid to be treated is transferred into the treatment unit 100 to obtain a certain volume of haemorrhagic fluid $V_T$ in the treatment bag 140, the result of the programme according to one or other of the examples of the second embodiment, notably when the fluid to be treated has to pass through the filtration device 110 before re-joining the treatment bag 140.

The measurement of the haematocrit level of the haemorrhagic fluid to be treated thus makes it possible to control the treatment in a finer manner, notably to optimise the sequences of concentration by filtration.

It has in particular been determined that the higher the haematocrit level of the haemorrhagic fluid to be treated, the greater the necessary washing volume. Furthermore, the washing volume is preferably also adjusted to reach a certain objective of elimination of compounds not desired for transfusion such as heparin.

Thus, if the haemorrhagic fluid to be treated has a high concentration of red blood cells, it is quickly going to reach the target haematocrit level at the outlet of the filtration device and the volume of blood to wash will be higher.

The treatment of the haemorrhagic fluid may comprise several successive steps to obtain the desired characteristics of the haemorrhagic fluid to re-transfuse according to the desired performances and which have been specified above in the description.

Thus, the method for treating haemorrhagic fluid comprises at least one phase of concentration of the haemorrhagic fluid to obtain the desired target haematocrit level. As specified above, this concentration step may consist in several successive steps of filtration and recirculation through the treatment bag and the recirculation line. It is called concentration by filtration.

Preferably, the treatment method comprises at least one dilution step, this dilution step consisting in adding to the volume of haemorrhagic fluid to be treated a determined volume of dilution fluid. As indicated above, this determined volume of dilution fluid is preferably calculated as a function of the measured haematocrit level of the haemorrhagic fluid to be treated and the target haematocrit level.

Further preferably, the dilution step is carried out before a step of concentration by filtration in order to increase the volume of haemorrhagic fluid to be treated and thus increase the volume of filtrate comprising compounds not desired for autotransfusion obtained during the step of concentration by filtration for a given target haematocrit level.

Once the haemorrhagic fluid to be treated has been circulated in the treatment unit 100, the first step of treatment is going to vary as a function of the measured haematocrit level for the haemorrhagic fluid to be treated and the target haematocrit level.

It may be advantageous to set a critical value of the initial haematocrit level of the haemorrhagic fluid to be treated so that at the outlet of the filtration device the haematocrit level is not greater than a critical value, which could increase haemolysis and clogging of the filtration device in the event of recirculation.

Thus, the first step of treatment may consist in a step of concentration by filtration carried out without prior dilution of the volume of haemorrhagic fluid to be treated. It could be possible in particular to begin the treatment in this way when the measured haematocrit level for the haemorrhagic fluid to be treated is less than a certain value, for example less than 35%.

The first step may alternatively consist in a simple step of filtration without concentration and without prior dilution of the volume of haemorrhagic fluid to be treated. It could be possible in particular to begin the treatment in this way when the measured haematocrit level for the haemorrhagic fluid to be treated is greater than or equal to a certain value, for example greater than or equal to 35%.

When the treatment system so allows, it may also be envisaged to begin by a dilution step preceding a step of concentration by filtration. Such a beginning will also be preferred when the haemorrhagic fluid to be treated has a high measured haematocrit level, for example greater than 35%.

When the measured haematocrit level for the haemorrhagic fluid to be treated is high (typically greater than or equal to 35%), it is in fact preferable not to carry out directly a cycle of concentration by filtration to avoid phenomena of haemolysis, cell degradation and clogging of the filtration device in the event of recirculation.

It is preferred to have several steps of concentration by filtration, where each step of concentration by filtration is preceded by a dilution step.

The number of steps of concentration by filtration and steps of dilution is optimised to minimise the overall treatment time of the haemorrhagic fluid to reach the target haematocrit level on the one hand, but also to obtain the desired performances of treatment, in particular with respect to the final concentration of compounds not desired for autotransfusion (such as heparin).

In a surprising manner, it has been discovered that it could be more efficient and faster, for a volume of haemorrhagic fluid to be treated with a given haematocrit level with a view to a target haematocrit level, to carry out several dilutions steps each followed by a step of concentration by filtration rather than a single step of concentration by filtration preceded by a dilution step.

Indeed, the fractionation of the overall treatment makes it possible to carry out shorter intermediate steps and to reduce in the end the overall treatment time for the same treatment performances. Fractionation is going to make it possible in fact to reduce the total dilution volume used for the treatment as a whole. There is thus better washing efficiency thanks to fractionation.

The table below illustrates the number of dilution steps and their characteristics as a function of the quantity of erythrocyte to wash for a haemorrhagic fluid to be treated having a starting haematocrit level of 15% for an end of treatment target of 50% and a starting concentration of heparin of 12 UI/ml for an end of treatment target of less than 0.5 UI/ml.

TABLE 1

| Quantity of erythrocyte to be treated (in ml) | | 100 | 150 | 200 | 250 |
|---|---|---|---|---|---|
| Total volume of dilution fluid for 1 wash (in ml) | 1 wash | 2310 | 3465 | 4620 | 5575 |
| Total volume of dilution fluid for 2 washes (in ml) | 2 washes | 796 | 1186 | 1580 | 1977 |
| Total volume of dilution fluid for 3 washes (in ml) | 3 washes | 541 | 802 | 1068 | 1336 |

It may be observed from these data that it is preferable to fractionate the overall wash to reduce overall the total dilution volume and thus the treatment time. Indeed, it is observed for example that to wash a volume of haemorrhagic fluid containing 150 ml of erythrocyte, it is more efficient to carry out two dilutions each preceding a concentration rather than a single dilution before concentration; the overall dilution volume is nearly three times lower, which will reduce by as much the treatment time.

Under the conditions illustrated above, it may be clearly seen that it is preferable to use two or three dilution steps rather than a single dilution step. If the difference in overall dilution volumes between several washing options is not great, the washing option involving the least washings may be chosen since this makes it possible to reduce the number of different steps in the overall treatment of the haemorrhagic fluid and thus to reduce the incompressible times existing between each of these different steps. Further, it should be recalled that the multiplicity of washings creates an additional risk for the quality of the cells and in particular a risk of haemolysis.

The number of dilution steps each followed by a concentration will thus be dependent on the total dilution volume accepted by the treatment system and as a function of the duration of treatment and the haemolytic factor that these successive dilutions and concentrations bring about.

In all cases, the dilution volume is a function on the one hand of the difference of substance to eliminate (thus the initial concentration and that to obtain), and on the other hand the volume and the haematocrit level of the concentrate to transfuse (thus the quantity of erythrocyte contained in the concentrate at a given haematocrit level).

The higher the volume of concentrate, haematocrit level, and substance concentration, the higher will be the washing volume and thus the more there is interest to choose a multiple sequence, and vice versa.

In a preferred manner, the proposed treatment method comprises two or three dilution steps each preceding a concentration step.

In practice, for small quantities of erythrocyte (for example less than 150 ml of erythrocyte) a sequence with 2 washings will be preferred, and for greater quantities of erythrocyte (for example greater than or equal to 150 ml of erythrocyte) a sequence with 3 washings could be preferable.

It is to be noted that it could be preferable to carry out a single dilution step preceding a concentration step, notably when the starting concentration of compounds not suitable for transfusion is low, for example when the starting concentration of heparin is less than 5 IU/ml, in particular less than 3 IU/ml.

As indicated above, the determined volume of dilution fluid for the dilution step is preferably calculated as a function of the measured haematocrit level of the haemorrhagic fluid to be treated and the target haematocrit level.

When the treatment is also parameterised to obtain a concentration of compounds not desired for autotransfusion less than a target concentration of compounds not desired for autotransfusion, said target concentration of compounds not desired for autotransfusion may also be used to calculate the determined volume of dilution fluid for the dilution step.

The initial concentration of compounds not desired for autotransfusion of the haemorrhagic fluid to be treated may also be used to calculate the determined volume of dilution fluid for the dilution step. It is appropriate in this case to be able to monitor the quantity of heparin having been introduced into the haemorrhagic fluid to be treated to deduce therefrom the concentration. This may be done by monitoring the flow rate of the device making it possible to inject heparin for example. This concentration may also be estimated as a function of existing clinical data and by taking for safety the maximum value that risks being found in the blood and that has to be eliminated.

When the treatment comprises several dilution steps each followed by a step of concentration by filtration then, during the final dilution step, the determined volume of dilution fluid is calculated as a function of the measured haematocrit level of said haemorrhagic fluid, the volume of haemorrhagic fluid to be treated, the target haematocrit level, and the target concentration of compounds not desired for autotransfusion.

In this case, during the preceding dilution steps, the determined volume of dilution fluid may be fixed. This dilution volume may in this case be fixed as a function of the characteristics of the treatment unit, in particular, a minimum volume of dilution fluid is chosen to avoid the phenomena of haemolysis of the haemorrhagic fluid and clogging of the filtration device. It is possible for example to fix a dilution volume comprised between 250 ml and 350 ml.

According to another possible embodiment, the determined volume of dilution fluid is calculated, for each successive dilution step, as a function of the measured haematocrit level of said haemorrhagic fluid, the volume of haemorrhagic fluid to be treated, the target haematocrit level, and the target concentration of compounds not desired for autotransfusion.

The higher the concentrate haematocrit target, the more is eliminated at each concentration an important quantity of compounds not desired for transfusion. There exists however a limit that it is preferable not to exceed so as not to damage the cells and in particular erythrocytes and cause haemolysis by destroying red blood cells.

Thus, for a sequence of treatment with two dilution steps each followed by a step of concentration by filtration, it could be possible for example to calculate the dilution volume of the first dilution step so as to eliminate at least 75% (for example 80%) of the undesired substances (for example heparin) contained in the concentrate. The dilution volume of the second dilution may be enslaved to the target concentration of undesired substances.

For a treatment sequence with three dilution steps each followed by a step of concentration by filtration, it could be possible for example to calculate the dilution volume of the first dilution step and the second dilution step so as to eliminate at least 65% (for example 66%) of undesired substances (for example heparin) contained in the preceding concentrate. The dilution volume of the third dilution may be enslaved to the target concentration of undesired substances.

The above parameters are particularly advantageous for a target haematocrit level of 50%.

D. Phase of Cleaning of the Filtration Device

During filtration on membrane, a drop in the filtration flow is generally observed throughout the process, during successive treatment cycles. This drop off in filtering capacity of the filtration membrane is due to several phenomena, notably to adsorption and to obstruction and clogging of the pores by the compounds to filter. Fouling by adsorption can represented losses of permeability going up to 90%, or even up to total blockage of the filtration.

The proposed treatment system, in particular the particular treatment unit 100 proposed in the present document, makes it possible to clean the filtration device 110 during treatment of a haemorrhagic fluid for a same patient, without having to dismantle said filtration device 110 from the treatment unit 100 and thus have an overall treatment of the haemorrhagic fluid not undergoing or undergoing few interruptions.

Several types of cleaning of the filtration device 110 may be envisaged with the proposed treatment system, these types of cleaning could be carried out alone or in addition to each other.

The first type of cleaning consists in rinsing the intake chamber 111 of the filtration device 110 which is carried out by introducing dilution fluid from the dilution unit 500 in the direction of the inlet 111a of the intake chamber 111 of the filtration device 110. This type of rinsing has already been described above in the final phase of the treatment cycle, before the effective transfer of the concentrate.

The second type of cleaning consists in rinsing the discharge chamber 112 of the filtration device 110 which is carried out by introducing dilution fluid from the dilution unit 500 in the direction of the inlet 112a of the discharge chamber 112 of the filtration device 110. This rinsing makes it possible to empty the discharge chamber 112 of filtrate which could still be present and to eliminate it to the recovery bag 310 via the discharge line 130. To do so, it is possible to close the clamps of the regulation valve 171 of the transfusion line 170 and the regulation valve 151 of the recirculation line 150, and the clamps of the regulation valve 191 of the dilution line 190 and the regulation valve 181 of the cleaning line 180 are opened. It is also preferable that the clamp of the regulation valve 152 of the recirculation line 150 is closed. The peristaltic pump is then started to circulate the dilution fluid in the direction of treatment of the dilution bag 500 to the filtration device 110.

The third type of cleaning consists in unclogging the filtration membrane 113 of the filtration device 110 through creation of a transmembrane counter-flow as has been mentioned above. To do so, the electric control valve 320 to stop the vacuum in the recovery unit 300 and the clamp of the regulation valve 131 of the discharge line 130 are closed. The clamps of the regulation valve 171 of the transfusion line 170, the regulation valve 151 of the recirculation line 150, and the regulation valve 152 of the recirculation line 150 are also closed, and the clamps of the regulation valve 191 of the dilution line 190 and the regulation valve 181 of the cleaning line 180 are opened. The fact that the discharge line 130 is obstructed, the pressure of cleaning fluid in the discharge chamber 112 increases and thus disbonds compounds being fixed on the filtration membrane 113. It is possible to control the pressure in this discharge chamber 112 by varying the drive speed of the pump 160 or by varying the flow passing at the level of the regulation valve 181 of the cleaning line 180.

Once the compounds have been disbonded from the filtration membrane 113, a rinsing of the discharge chamber 112 may be carried out as previously, by opening the clamp of the regulation valve 131 of the discharge line 130. It is to be noted that the unclogging flow rate, that is to say the flow rate of circulation of the cleaning fluid to create the transmembrane counter-flow, is preferably at least equal to the treatment flow rate, that is to say the circulation flow rate of the haemorrhagic fluid in the treatment unit 100. It has in fact been observed that this would make it possible to have faster overall treatment times while reducing the loss of red blood cells at each cycle. The loss of red blood cells is for example only 5% compared to 10% when the unclogging flow rate goes from 1200 ml/min to 600 ml/min. The performance of cleaning the fibre is also improved.

The three types of cleaning described above may be carried out alone or in combination, one after the other.

For example, the following cleaning sequence in two stages may be envisaged:

a1. unclogging the filtration membrane 113 of the filtration device 110 according to the third type of cleaning above, notably to clean the filtration membrane from the outside to the inside; then b1. rinsing the intake chamber 111 of the filtration device 110 according to the above first type of cleaning.

According to another example, the following cleaning sequence in three stages may be envisaged:

a1. rinsing the intake chamber 111 of the filtration device 110 according to the first type of cleaning above; then b2. unclogging the filtration membrane 113 of the filtration device 110 according to the third type of cleaning above, notably to clean the filtration membrane from the outside to the inside; then c2. rinsing the intake chamber 111 of the filtration device 110 according to the above first type of cleaning.

Once the filtration device 110 has been cleaned, it is possible to adjust the dilution volume present in the treatment chamber 140, this dilution volume being able to be used for a subsequent treatment cycle as explained above with reference to the preparatory phase of the treatment cycle. Thus, after a cleaning phase, it is advisable to close the clamp of the regulation valve 181 of the cleaning line 180 while maintaining closed the clamp of the regulation valve 131 of the discharge line 130, and the clamp of the regulation valve 152 of the recirculation line 150 is opened while continuing to circulate dilution fluid with the pump 160.

The invention claimed is:

1. A method for treating, by filtration, haemorrhagic fluid contained in a container with a view to subsequent autotransfusion, comprising at least one step of concentration by filtration of said haemorrhagic fluid in order to increase the concentration of red blood cells in the haemorrhagic fluid to reach a target haematocrit level while at the same time removing from the haemorrhagic fluid a filtrate comprising compounds not desired for autotransfusion, characterised in that it further comprises the following steps:
   a preliminary step of measuring the haematocrit level of the haemorrhagic fluid; and
   a dilution step consisting in adding to the volume of haemorrhagic fluid to be treated a determined volume of dilution fluid, said determined volume of dilution fluid being calculated as a function of the measured haematocrit level of said haemorrhagic fluid and the target haematocrit level;
   wherein the treatment is further parameterised to obtain a concentration of compounds not desired for autotransfusion less than a target concentration of compounds not desired for autotransfusion, said target concentration of compounds not desired for autotransfusion also being used to calculate the determined volume of dilution fluid for the dilution step.

2. The method of claim 1, wherein the dilution step is carried out before the at least one step of concentration by filtration in order to increase the volume of haemorrhagic fluid to be treated and thus increase the volume of filtrate comprising compounds not desired for autotransfusion obtained during the step of concentration by filtration for a given target haematocrit level.

3. The method of Method according to claim 1, wherein the initial concentration of compounds not desired for autotransfusion of the haemorrhagic fluid to be treated is also used to calculate the determined volume of dilution fluid for the dilution step.

4. The method of claim 1, wherein the number of steps of concentration by filtration and dilution steps is optimised to minimise the overall treatment time of the haemorrhagic fluid, the optimisation being achieved by fixing a maximum value of volume of dilution fluid used for each dilution step and by increasing the number of concentration by filtration steps.

5. The method of Method according to claim 1, comprising several steps of concentration by filtration each being preceded by a dilution step, wherein during the final dilution step the determined volume of dilution fluid is calculated as a function of the measured haematocrit level of said haemorrhagic fluid, the volume of haemorrhagic fluid to be treated, the target haematocrit level, and the target concentration of compounds not desired for autotransfusion, whereas during the preceding dilution steps, the determined volume of dilution fluid is fixed.

6. The method of claim 1, comprising several steps of concentration by filtration each being preceded by a dilution step, wherein for each dilution step the determined volume of dilution fluid is calculated as a function of the measured haematocrit level of said haemorrhagic fluid, the volume of haemorrhagic fluid to be treated, the target haematocrit level, and the target concentration of compounds not desired for autotransfusion.

7. The method of to claim 1, comprising at least two steps of concentration by filtration each being preceded by a dilution step.

8. The method of to claim 1, comprising at least three steps of concentration by filtration each being preceded by a dilution step.

9. The method of to claim 8, wherein the dilution volume of the first dilution step preceding the first concentration step is provided to eliminate at least 65% of compounds not desired for autotransfusion present in the haemorrhagic fluid before the first dilution and concentration steps, and the dilution volume of the second dilution step preceding the second concentration step is also provided to eliminate at least 65% of compounds not desired for autotransfusion present in the haemorrhagic fluid before the second dilution and concentration steps.

10. The method of to claim 1, comprising a first step of concentration by filtration carried out without prior dilution of the volume of haemorrhagic fluid to be treated, followed at least by a dilution step and a step of concentration by filtration.

11. The method of to claim 1, comprising a first simple filtration step without concentration and without prior dilution of the volume of haemorrhagic fluid to be treated, followed at least by a dilution step and a step of concentration by filtration.

12. The method of to claim 1, wherein the volume of haemorrhagic fluid to be treated is determined as a function of the measured haematocrit level of said haemorrhagic fluid and the target haematocrit level.

13. A system for treating a haemorrhagic fluid with a view to autotransfusion, including a unit for treating the haemorrhagic fluid, said treatment unit comprising:
   a filtration device comprising a filtration membrane for tangential filtration arranged in a case in such a way as to separate an intake chamber from a discharge chamber, the intake chamber and the discharge chamber each having an inlet and an outlet for fluids;
   a treatment bag having an inlet and an outlet fluidically connected by a recirculation line to the outlet and to the inlet of the intake chamber of the filtration device, respectively, enabling circulation of haemorrhagic fluid in the recirculation line in a direction going from the outlet of the treatment bag to the inlet of the treatment bag through the intake chamber of the filtration device;

an intake line fluidically connected to the recirculation line between the outlet of the treatment bag and the inlet of the intake chamber of the filtration device making it possible to supply the treatment unit with collected haemorrhagic fluid with a view to filtration through the filtration membrane of the filtration device in order to remove from the haemorrhagic fluid a filtrate comprising compounds not desired for autotransfusion;

a transfusion line fluidically connected to the recirculation line between the outlet of the treatment bag and the inlet of the intake chamber of the filtration device making it possible to recover the treated haemorrhagic fluid contained in said treatment bag;

a discharge line fluidically connected to the outlet of the discharge chamber of the filtration device so as to discharge the filtrate having traversed the filtration membrane from the intake chamber;

characterised in that the treatment unit further comprises:
- a first flow regulation member arranged for flow regulation in the recirculation line at the outlet of the treatment bag,
- a dilution line configured to convey a dilution fluid into the treatment unit, the dilution line being fluidically connected to the recirculation line at a position between the outlet of the treatment bag and the inlet of the intake chamber of the filtration device, a haematocrit sensor arranged to measure a haematocrit level of the haemorrhagic fluid circulating in the treatment unit, and in that the treatment system further comprises a device for controlling the dilution line programmed to control the dilution fluid to convey into the treatment unit as a function of the haematocrit level measured by the haematocrit sensor.

14. A method for treating, by filtration, haemorrhagic fluid contained in a container with a view to subsequent autotransfusion, comprising at least one step of concentration by filtration of said haemorrhagic fluid in order to increase the concentration of red blood cells in the haemorrhagic fluid to reach a target haematocrit level while at the same time removing from the haemorrhagic fluid a filtrate comprising compounds not desired for autotransfusion, characterised in that it further comprises the following steps:
- a preliminary step of measuring the haematocrit level of the haemorrhagic fluid; and
- a dilution step consisting in adding to the volume of hemorrhagic fluid to be treated a determined volume of dilution fluid, said determined volume of dilution fluid being calculated as a function of the measured haematocrit level of said haemorrhagic fluid and the target haematocrit level;
- wherein the method comprises at least two steps of concentration by filtration each being preceded by a dilution step, the dilution volume of the first dilution step preceding the first concentration step being provided to eliminate at least 75% of compounds not desired for autotransfusion present in the haemorrhagic fluid before the first steps of dilution and concentration.

15. The method of claim 14, comprising at least three steps of concentration by filtration each being preceded by a dilution step, wherein the dilution volume of the first dilution step preceding the first concentration step is provided to eliminate at least 65% of compounds not desired for autotransfusion present in the haemorrhagic fluid before the first dilution and concentration steps, and the dilution volume of the second dilution step preceding the second concentration step is also provided to eliminate at least 65% of compounds not desired for autotransfusion present in the haemorrhagic fluid before the second dilution and concentration steps.

16. A method for treating, by filtration, haemorrhagic fluid contained in a container with a view to subsequent autotransfusion, comprising at least one step of concentration by filtration of said haemorrhagic fluid in order to increase the concentration of red blood cells in the haemorrhagic fluid to reach a target haematocrit level while at the same time removing from the haemorrhagic fluid a filtrate comprising compounds not desired for autotransfusion, characterised in that it further comprises the following steps:
- a preliminary step of measuring the haematocrit level of the haemorrhagic fluid; and
- a dilution step consisting in adding to the volume of haemorrhagic fluid to be treated a determined volume of dilution fluid, said determined volume of dilution fluid being calculated as a function of the measured haematocrit level of said haemorrhagic fluid and the target haematocrit level;
- wherein the method comprises a first step of simple filtration without concentration and without prior dilution of the volume of haemorrhagic fluid to be treated, followed at least by a dilution step and a step of concentration by filtration.

17. A method for treating, by filtration, haemorrhagic fluid contained in a container with a view to subsequent autotransfusion, comprising at least one step of concentration by filtration of said haemorrhagic fluid in order to increase the concentration of red blood cells in the haemorrhagic fluid to reach a target haematocrit level while at the same time removing from the haemorrhagic fluid a filtrate comprising compounds not desired for autotransfusion, characterised in that it further comprises the following steps:
- a preliminary step of measuring the haematocrit level of the haemorrhagic fluid; and
- a dilution step consisting in adding to the volume of haemorrhagic fluid to be treated a determined volume of dilution fluid, said determined volume of dilution fluid being calculated as a function of the measured haematocrit level of said haemorrhagic fluid and the target haematocrit level;
- wherein the method further comprises a first treatment step for which:
  - if the haematocrit level of the haemorrhagic fluid is greater than a threshold haematocrit level value, the first step of the treatment consists in a simple filtration without concentration and without prior dilution of the volume of haemorrhagic fluid to be treated; and
  - if the haematocrit level of the haemorrhagic fluid is less than or equal to the threshold haematocrit level value, the first step of the treatment consists in a concentration by filtration without prior dilution of the volume of haemorrhagic fluid to be treated.

\* \* \* \* \*